(12) United States Patent
Rosario-Jansen et al.

(10) Patent No.: US 11,639,927 B2
(45) Date of Patent: *May 2, 2023

(54) METHODS AND KITS FOR PREDICTING INFUSION REACTION RISK AND ANTIBODY-MEDIATED LOSS OF RESPONSE BY MONITORING SERUM URIC ACID DURING PEGYLATED URICASE THERAPY

(71) Applicant: Horizon Therapeutics USA, Inc., Deerfield, IL (US)

(72) Inventors: Theresa Rosario-Jansen, Randolph, NJ (US); David Erick Wright, Ramona, CA (US)

(73) Assignee: Horizon Therapeutics USA, Inc., Deerfield, IL (US)

( * ) Notice: Subject to any disclaimer, the term of this patent is extended or adjusted under 35 U.S.C. 154(b) by 166 days.

This patent is subject to a terminal disclaimer.

(21) Appl. No.: 17/036,110

(22) Filed: Sep. 29, 2020

(65) Prior Publication Data

US 2021/0181187 A1 Jun. 17, 2021

Related U.S. Application Data

(63) Continuation of application No. 16/195,446, filed on Nov. 19, 2018, now Pat. No. 10,823,727, which is a continuation of application No. 15/906,839, filed on Feb. 27, 2018, now Pat. No. 10,139,399, which is a continuation of application No. 15/165,318, filed on May 26, 2016, now abandoned, which is a continuation of application No. 13/379,704, filed as application No. PCT/US2010/004008 on Jun. 25, 2010, now Pat. No. 9,377,454.

(60) Provisional application No. 61/298,718, filed on Jan. 27, 2010, provisional application No. 61/248,698, filed on Oct. 5, 2009, provisional application No. 61/269,669, filed on Jun. 25, 2009.

(51) Int. Cl.
| | | |
|---|---|---|
| C12Q 1/62 | (2006.01) |
| G01N 33/53 | (2006.01) |
| G01N 33/68 | (2006.01) |
| C12N 9/02 | (2006.01) |
| A61K 47/60 | (2017.01) |
| A61P 19/02 | (2006.01) |
| A61K 9/00 | (2006.01) |
| A61K 38/44 | (2006.01) |

(52) U.S. Cl.
CPC ....... *G01N 33/5308* (2013.01); *A61K 9/0019* (2013.01); *A61K 38/44* (2013.01); *A61K 47/60* (2017.08); *A61P 19/02* (2018.01); *C12Y 107/03003* (2013.01); *G01N 33/6893* (2013.01); *G01N 2333/90694* (2013.01); *G01N 2800/107* (2013.01); *G01N 2800/52* (2013.01); *G01N 2800/56* (2013.01)

(58) Field of Classification Search
CPC .......... G01N 2800/52; G01N 33/6893; G01N 2800/107; G01N 33/5308; G01N 2333/90694; G01N 2800/56; A61K 38/44; A61K 9/0019; A61K 47/60; C12Y 107/03003; A61P 19/02
See application file for complete search history.

(56) References Cited

U.S. PATENT DOCUMENTS

| | | |
|---|---|---|
| 1,141,973 A | 6/1915 | Nichols |
| 3,451,996 A | 6/1969 | Sumyk |
| 3,613,231 A | 10/1971 | Pugh |
| 3,616,231 A | 10/1971 | Bergmeyer |
| 3,931,399 A | 1/1976 | Bohn |
| 4,027,676 A | 6/1977 | Mattei |
| 4,064,010 A | 12/1977 | Harris |
| 4,141,973 A | 2/1979 | Balazs |
| 4,169,764 A | 10/1979 | Masaharu |
| 4,179,337 A | 12/1979 | Davis |
| 4,251,431 A | 2/1981 | Carswell |
| 4,297,344 A | 10/1981 | Schwinn |
| 4,301,153 A | 11/1981 | Rosenberg |
| 4,312,979 A | 1/1982 | Takemoto |
| 4,315,852 A | 2/1982 | Leibowitz |
| 4,317,878 A | 3/1982 | Nakanishi |
| 4,343,735 A | 8/1982 | Menge |
| 4,343,736 A | 8/1982 | Uemura |
| 4,376,110 A | 3/1983 | David |
| 4,421,650 A | 12/1983 | Nagasawa |
| 4,425,431 A | 1/1984 | Takemoto |
| 4,445,745 A | 5/1984 | Cartesse |

(Continued)

FOREIGN PATENT DOCUMENTS

| | | |
|---|---|---|
| AU | 5251599 A | 2/2000 |
| BE | 837379 A | 7/1976 |

(Continued)

OTHER PUBLICATIONS

"Aggregate", Stedman's Medical Dictionary, 27th Edition, PDR Electronic Library, accessed on Jun. 10, 2009 at http://www.thomsonhe.com/pdrel/librarian/ND.

(Continued)

*Primary Examiner* — Satyendra K Singh

(74) *Attorney, Agent, or Firm* — Cooley LLP

(57) ABSTRACT

Methods and kits for predicting infusion reaction risk and antibody-mediated loss of response during intravenous PEGylated uricase therapy in gout patients is provided. Routine SUA monitoring can be used to identify patients receiving PEGylated uricase who may no longer benefit from treatment and who are at greater risk for infusion reactions.

9 Claims, 6 Drawing Sheets

(56) References Cited

U.S. PATENT DOCUMENTS

| | | |
|---|---|---|
| 4,450,103 A | 5/1984 | Konrad |
| 4,460,575 A | 7/1984 | D Hinterland |
| 4,460,683 A | 7/1984 | Gloger |
| 4,485,176 A | 11/1984 | Bollin, Jr. |
| 4,753,796 A | 6/1988 | Moreno |
| 4,766,106 A | 8/1988 | Katre |
| 4,797,474 A | 1/1989 | Patroni |
| 4,816,567 A | 3/1989 | Cabilly |
| 4,847,079 A | 7/1989 | Kwan |
| 4,847,325 A | 7/1989 | Shadle |
| 4,917,888 A | 4/1990 | Katre |
| 4,945,086 A | 7/1990 | Benitz |
| 4,946,778 A | 8/1990 | Ladner |
| 4,966,963 A | 10/1990 | Patroni |
| 4,987,076 A | 1/1991 | Takashio |
| 4,992,531 A | 2/1991 | Patroni |
| 5,008,377 A | 4/1991 | Patroni |
| 5,010,183 A | 4/1991 | Macfarlane |
| 5,114,916 A | 5/1992 | Shirahata |
| 5,122,614 A | 6/1992 | Zalipsky |
| 5,225,539 A | 7/1993 | Winter |
| 5,283,317 A | 2/1994 | Saifer |
| 5,286,637 A | 2/1994 | Veronese |
| 5,362,641 A | 11/1994 | Fuks |
| 5,382,518 A | 1/1995 | Caput |
| 5,428,128 A | 6/1995 | Mensi-Fattohi |
| 5,458,135 A | 10/1995 | Patton |
| 5,468,478 A | 11/1995 | Saifer |
| 5,529,915 A | 6/1996 | Phillips |
| 5,541,098 A | 7/1996 | Caput |
| 5,567,422 A | 10/1996 | Greenwald |
| 5,585,089 A | 12/1996 | Queen |
| 5,612,460 A | 3/1997 | Zalipsky |
| 5,624,903 A | 4/1997 | Mueller |
| 5,633,227 A | 5/1997 | Muller |
| 5,637,749 A | 6/1997 | Greenwald |
| 5,643,575 A | 7/1997 | Martinez |
| 5,653,974 A | 8/1997 | Hung |
| 5,711,944 A | 1/1998 | Gilbert |
| 5,762,923 A | 6/1998 | Gross |
| 5,766,897 A | 6/1998 | Braxton |
| 5,811,096 A | 9/1998 | Aleman |
| 5,816,397 A | 10/1998 | Pratt |
| 5,824,784 A | 10/1998 | Kinstler |
| 5,880,255 A | 3/1999 | Delgado |
| 5,919,455 A | 7/1999 | Greenwald |
| 5,929,231 A | 7/1999 | Maelkki |
| 5,932,462 A | 8/1999 | Harris |
| 5,948,668 A | 9/1999 | Hartman |
| 5,955,336 A | 9/1999 | Shigyo |
| 6,006,753 A | 12/1999 | Efendic |
| 6,130,318 A | 10/2000 | Wild |
| 6,201,110 B1 | 3/2001 | Olsen |
| 6,211,341 B1 | 4/2001 | Zeelon |
| 6,245,901 B1 | 6/2001 | Von |
| 6,468,210 B2 | 10/2002 | Iliff |
| 6,475,143 B2 | 11/2002 | Iliff |
| 6,524,241 B2 | 2/2003 | Iliff |
| 6,527,713 B2 | 3/2003 | Iliff |
| 6,569,093 B2 | 5/2003 | Iliff |
| 6,575,235 B2 | 6/2003 | Zupanick |
| 6,576,235 B1 | 6/2003 | Williams |
| 6,608,892 B2 | 8/2003 | Shaffer |
| 6,783,965 B1 | 8/2004 | Sherman |
| 6,913,915 B2 | 7/2005 | Ensor |
| 7,056,713 B1 | 6/2006 | Hershfield |
| 7,723,089 B2 | 5/2010 | Williams |
| 7,811,800 B2 | 10/2010 | Hartman |
| 7,927,589 B2 | 4/2011 | Williams |
| 7,927,852 B2 | 4/2011 | Sherman |
| 7,964,381 B2 | 6/2011 | Hartman |
| 8,034,594 B2 | 10/2011 | Hartman |
| 8,067,553 B2 | 11/2011 | Williams |
| 8,148,123 B2 | 4/2012 | Hartman |
| 8,178,334 B2 | 5/2012 | Hartman |
| 8,188,224 B2 | 5/2012 | Hartman |
| 8,293,228 B2 | 10/2012 | Hartman |
| 8,465,735 B2 | 6/2013 | Hartman |
| 8,541,205 B2 | 9/2013 | Hartman |
| 8,618,267 B2 | 12/2013 | Williams |
| 8,913,915 B2 | 12/2014 | Makino |
| 8,921,064 B2 | 12/2014 | Sherman |
| 9,017,980 B2 | 4/2015 | Hartman |
| 9,377,454 B2 | 6/2016 | Rosario-Jansen |
| 9,402,827 B2 | 8/2016 | Miner |
| 9,534,013 B2 | 1/2017 | Fischer |
| 9,670,467 B2 | 6/2017 | Hartman |
| 9,885,024 B2 | 2/2018 | Williams |
| 9,926,537 B2 | 3/2018 | Hartman |
| 9,926,538 B2 | 3/2018 | Hartman |
| 10,139,399 B2 | 11/2018 | Rosario-Jansen et al. |
| 10,160,958 B2 | 12/2018 | Hartman |
| 10,731,139 B2 | 8/2020 | Hartman |
| 10,823,727 B2 | 11/2020 | Rosario-Jansen |
| 11,345,899 B2 | 5/2022 | Hartman et al. |
| 2002/0010319 A1 | 1/2002 | Ansaldi |
| 2002/0151703 A1 | 10/2002 | Yokoyama |
| 2003/0082786 A1 | 5/2003 | Ensor |
| 2003/0166249 A1 | 9/2003 | Williams |
| 2005/0014240 A1 | 1/2005 | Sherman |
| 2005/0084478 A1 | 4/2005 | Liu |
| 2006/0188971 A1 | 8/2006 | Hershfield |
| 2007/0274977 A1 | 11/2007 | Hartman |
| 2008/0031864 A1 | 2/2008 | Williams et al. |
| 2008/0057048 A1 | 3/2008 | Sherman et al. |
| 2008/0145876 A1 | 6/2008 | Armstrong |
| 2008/0159976 A1 | 7/2008 | Hartman |
| 2009/0023715 A1 | 1/2009 | Brown |
| 2009/0169534 A1 | 7/2009 | Hartman |
| 2009/0209021 A1 | 8/2009 | Hartman |
| 2009/0317889 A1 | 12/2009 | Fischer |
| 2010/0152305 A1 | 6/2010 | Cedarbaum |
| 2010/0323422 A1 | 12/2010 | Williams |
| 2010/0323423 A1 | 12/2010 | Williams |
| 2011/0104751 A1 | 5/2011 | Hartman |
| 2011/0217755 A1 | 9/2011 | Hartman |
| 2011/0287466 A1 | 11/2011 | Sherman et al. |
| 2012/0070876 A1 | 3/2012 | Hartman |
| 2012/0149083 A1 | 6/2012 | Williams |
| 2012/0225046 A1 | 9/2012 | Hartman |
| 2012/0301454 A1 | 11/2012 | Rosario-Jansen |
| 2012/0309085 A1 | 12/2012 | Hartman |
| 2013/0052677 A1 | 2/2013 | Williams et al. |
| 2013/0084273 A1 | 4/2013 | Hartman |
| 2013/0330803 A1 | 12/2013 | Hartman |
| 2014/0363414 A1 | 12/2014 | Sherman |
| 2015/0197732 A1 | 7/2015 | Hartman |
| 2016/0035091 A1 | 2/2016 | Kubassova |
| 2016/0158318 A1 | 6/2016 | Cohen |
| 2016/0160188 A1 | 6/2016 | Williams et al. |
| 2016/0377604 A1 | 12/2016 | Rosario-Jansen |
| 2017/0166873 A1 | 6/2017 | Fischer |
| 2017/0258927 A1 | 9/2017 | Johnston |
| 2017/0298326 A1 | 10/2017 | Hartman et al. |
| 2017/0313993 A1 | 11/2017 | Hartman |
| 2017/0313994 A1 | 11/2017 | Hartman |
| 2017/0313995 A1 | 11/2017 | Hartman et al. |
| 2017/0321193 A1 | 11/2017 | Hartman et al. |
| 2018/0008665 A1 | 1/2018 | Qiao |
| 2018/0127432 A1 | 5/2018 | Trzupek |
| 2018/0188242 A1 | 7/2018 | Rosario-Jansen |
| 2018/0223263 A1 | 8/2018 | Sherman |
| 2018/0289776 A1 | 10/2018 | Johnston |
| 2019/0316097 A1 | 10/2019 | Hartman et al. |
| 2019/0317083 A1 | 10/2019 | Rosario-Jansen et al. |
| 2020/0056160 A1 | 2/2020 | Fischer |
| 2020/0237879 A1 | 7/2020 | Kent et al. |
| 2020/0237880 A1 | 7/2020 | Kent et al. |
| 2020/0237881 A1 | 7/2020 | Kent et al. |
| 2020/0353057 A1 | 11/2020 | Kent |
| 2021/0079362 A1 | 3/2021 | Hartman et al. |

(56) References Cited

U.S. PATENT DOCUMENTS

2022/0323445 A1 10/2022 Peloso et al.
2022/0323550 A1 10/2022 Peloso

FOREIGN PATENT DOCUMENTS

| | | |
|---|---|---|
| CA | 2193993 A1 | 1/1996 |
| CN | 1322141 A | 11/2001 |
| CN | 1322243 A | 11/2001 |
| CN | 101168052 A | 4/2008 |
| CN | 101198693 A | 6/2008 |
| CN | 104066324 A | 9/2014 |
| DE | 837379 | 8/1955 |
| DE | 279486 A1 | 6/1990 |
| DE | 279486 C | 6/1990 |
| DE | 279489 A1 | 6/1990 |
| EP | 0028033 A2 | 5/1981 |
| EP | 0034307 A2 | 8/1981 |
| EP | 0043980 A2 | 1/1982 |
| EP | 0055188 A1 | 6/1982 |
| EP | 0204283 A2 | 12/1986 |
| EP | 0226448 A2 | 6/1987 |
| EP | 0279486 A2 | 8/1988 |
| EP | 0321134 A2 | 6/1989 |
| EP | 0408461 | 1/1991 |
| EP | 0727437 A2 | 8/1996 |
| EP | 1100542 A2 | 5/2001 |
| EP | 1100880 | 5/2001 |
| EP | 2349280 A1 | 8/2011 |
| JP | S5599189 A | 7/1980 |
| JP | 55135590 A | 10/1980 |
| JP | S57192435 A | 11/1982 |
| JP | S6255079 A | 3/1987 |
| JP | S62223192 A | 10/1987 |
| JP | H01216939 A | 8/1989 |
| JP | H0354581 A | 3/1991 |
| JP | H03148298 A | 6/1991 |
| JP | H06255079 A | 9/1994 |
| JP | H09154581 A | 6/1997 |
| JP | H10500565 A | 1/1998 |
| JP | H10502360 A | 3/1998 |
| JP | 1999075876 | 3/1999 |
| JP | 3148208 B2 | 3/2001 |
| JP | 3148298 B2 | 3/2001 |
| JP | 2002522399 A | 7/2002 |
| JP | 2002524053 A | 8/2002 |
| JP | 2003521937 A | 7/2003 |
| JP | 2005241424 A | 9/2005 |
| JP | 2008505656 A | 2/2008 |
| JP | 2008535499 A | 9/2008 |
| JP | 2008535500 A | 9/2008 |
| JP | 5599189 A | 11/2009 |
| JP | 2013009960 A | 1/2013 |
| JP | 5599189 | 10/2014 |
| KR | 100333148 B1 | 9/1994 |
| KR | 0159107 B1 | 11/1998 |
| KR | 488848 | 2/2000 |
| KR | 100365606 B1 | 6/2000 |
| KR | 100318706 | 12/2001 |
| KR | 100369838 | 1/2003 |
| KR | 19980069019 | 9/2003 |
| KR | 100488848 B1 | 5/2005 |
| RU | 2001103131 A | 8/1999 |
| RU | 2246318 C2 | 2/2005 |
| RU | 2281954 C2 | 8/2006 |
| WO | 8604145 A1 | 7/1986 |
| WO | 8700056 A1 | 1/1987 |
| WO | 9216221 A1 | 10/1992 |
| WO | 9419007 A1 | 9/1994 |
| WO | 9419470 A1 | 9/1994 |
| WO | 9423735 A1 | 10/1994 |
| WO | 9423740 A1 | 10/1994 |
| WO | 9511987 A1 | 5/1995 |
| WO | 9525785 A1 | 9/1995 |
| WO | 9601274 A1 | 1/1996 |
| WO | 9623064 A1 | 8/1996 |
| WO | 9808873 A1 | 3/1998 |
| WO | 9831383 A1 | 7/1998 |
| WO | 2000007629 A2 | 2/2000 |
| WO | 2000008196 A2 | 2/2000 |
| WO | WO-0008196 A3 | 3/2000 |
| WO | 0159078 A2 | 8/2001 |
| WO | 2002070007 | 9/2002 |
| WO | 03011211 A2 | 2/2003 |
| WO | 03045436 A1 | 6/2003 |
| WO | 2004092393 | 10/2004 |
| WO | 2004092393 A1 | 10/2004 |
| WO | 2005110386 | 11/2005 |
| WO | 2006110761 A2 | 10/2006 |
| WO | 2006110819 A2 | 10/2006 |
| WO | 2007100741 | 9/2007 |
| WO | 2008051178 A2 | 5/2008 |
| WO | WO-2010071865 A1 | 6/2010 |
| WO | 2010151823 A1 | 12/2010 |
| WO | WO-2011032175 A1 | 3/2011 |
| WO | WO-2013066353 A1 | 5/2013 |
| WO | 2018089808 | 5/2018 |
| WO | 2020160322 | 8/2020 |
| WO | 2020160324 | 8/2020 |
| WO | 2020160325 | 8/2020 |
| WO | WO-2022035828 A1 | 2/2022 |

OTHER PUBLICATIONS

"Amino Acid Sequence of Amino Truncated Chimeric Pig-Baboon Uricase", Retrieved from EBI Accession No. GSP: AAY69153, XP002404207, May 30, 2000.

"Designing Custom Peptides," from SIGMA Genosys, pp. 1-2. Accessed Dec. 16, 2004.

"Dimer", Stedman's Medical Dictionary, 27th Edition, PDR Electronic Library, accessed Jun. 10, 2009 at http://www.thomsonhe.com/pdrel/librarian/ND.

"How to Control Uric Acid Levels" from http://www.top10homeremedies.com/how-to/control-uric-acid-levels.html, pp. 1-6. Accessed Sep. 22, 2015.

"N- and C-Terminally Truncated Pig-Baboon Chimeric Uricase (PBC-NT-CT)", Retrieved from EBI Accession No. GSP: AAY81255, XP002404208, Jun. 19, 2000.

"Short Protocols in Molecular Biology", John Wiley & Sons, (1997).

A list of GenBank Accession Numbers corresponding to Uricase Family Member Sequences submitted by Applicants to the Examiner in corresponding South Korean Appl. No. 2001-7001569 on Aug. 24, 2004.

Abstract submitted to ACR in 2020 (noted in powerpoint slide deck used for preparing CIP).

Abuchowski, A. et al., "Effect of Covalent Attachment of Polyethylene Glycol On Immunogenicity and Circulating Life of Bovine Liver Catalase," J. Biol. Chem. 252:3582-3586, American Society for Biochemistry and Molecular Biology, United States (1977).

Abuchowski, A. et al., "Reduction of Plasma Urate Levels in the Cockerel with Polyethylene Glycol-Uricase," J. Pharmacol. Exp. Ther. 219:352-354, The American Society for Pharmacology and Experimental Therapeutics, United States (1981).

Adams, P. et al., "Current Estimates From the National Health Interview Survey, 1996", Vital Health Study, (200):1-203, (1999).

Al-Shawi et al., "A Novel Immunoradiometric Assay for Human Liver Ferritin", J. Clin. Pathol., 36(4), pp. 440-444, Abstract only, (1983).

Alamillo, J. et al, "Purification and molecular properties of urate oxidase from Chlamydomonas reinhardtii," Biochim. Biophys. Acta 1076 :203-208, Elsevier Science Publishers B.V., Netherlands (1991).

Alvares, K. et al., "Rat urate oxidase produced by recombinant baculovirus expression: formation of peroxisome crystalloid core-like structures", Proc. Natl. Acad. Sci. USA 89:4908-4912, National Academy of Sciences, United States, (1992).

Alvares, K. et al., "The Nucleotide Sequence of a Full Length cDNA Clone Encoding Rat Liver Urate Oxidase," Biochem. Biophys. Res. Commun. 158:991-995, Academic Press, Inc., United States, (1989).

(56) References Cited

OTHER PUBLICATIONS

Antonopoulos, C. et al., "The Precipitation of Polyanions by Long-Chain Aliphatic Ammonium Compounds", Biochim. Biophys. Acta 54:213-226, (1961).

Augustsson, J. et al., "Low-Dose Glucocorticoid Therapy Decreases Risk for Treatment-Limiting Infusion Reaction to Infliximab in Patients with Rheumatoid Arthritis", Extended Report, Ann. Rheum. Dis., vol. 66, pp. 1462-1466, (2007).

Baraf H. et al., "Resolution Of Tophi With Intravenous Peg-uricase In Refractory Gout", Arthritis & Rheumatism, 2005, Sep Supplement, vol. 52, No. 9, p. S105.

Baraf H. et al., "Resolution of Tophi With Intravenous Peg-uricase in Treatment-Failure Gout", presented at the EULAR—Annual European Congress of Rheumatology, on Jun. 21-24, 2006 at Amsterdam, Netherlands, Poster 465.

Baraf, H. et al. "Arthritis & Rheumatism", The Official Journal of the American College Of Rheumatology Abstract Supplement, vol. 52, No. 9, p. S105 (Abstract 194) previously submitted as Lee et al., (Sep. 2005) as "Arthritis & Rheumatism" in The Official Journal Of The American College Of Rheumatology Abstract Supplement, vol. 52, No. 9, p. S105.

Baraf, H. et al., "Tophus Burden Reduction With Pegloticase: Results From Phase 3 Randomized Trials and Open-Label Extension in Patients With Chronic Gout Refractory to Conventional Therapy", Arthritis Res Ther., 15(5):R137, (2013).

Baraf, H. et al., "Resolution of Tophi With Intravenous Peg-uricase in Refractory Gout", presented at American College of Rheumatology 2005 Annual Scientific Meeting on Nov. 13-17, 2005 at San Diego, CA, Poster 194.

Bayat S. etal., Development of a Dual-Energy Computed Tomography Scoring System for Measurement of Urate Deposition in Gout, Arthritis Care & Research, vol. 68, No. 6, Jun. 2016, pp. 769-775.

Becker, M. et al., "Activation of Hydroxylic Polymers—by Reaction with Carbonate or Chloroformate Ester in Presence", English Abstract, Derwent World Patents Index, Accession No. 8448552, (2004).

Becker, M. et al., "Febuxocat Compared with Allopurinol in Patients with Hyperuricemia and Gout", N. Engl. J. Med., 353(23): 2450-2461, (2005).

Becker, M., "Hyperuricemia and Gout", The Metabolic and Molecular Bases of Inherited Disease. Edited by Scriver CR, Beaudet AL, Sly WS, Valle D, 8th edn. New York; McGraw-Hill; 2513-2535, (2001).

Ben-Bassat, A. and Bauer, K., "Amino-Terminal Processing of Proteins," Nature vol. 326, p. 315, (1987).

Ben-Bassat, A. et al., "Processing of the Initiation Methionine from Proteins: Properties of the *Escherichia coli* Methionine Aminopeptidase and Its Gene Structure," Journal of Bacteriology, vol. 169, No. 2, p. 751-757, (1987).

Benbacer, L. et al., "Interspecies aminopeptidase-N chimeras reveal species-specific receptor recognition by canine coronavirus, feline infectious peritonitis virus, and transmissible gastroenteritis virus", J Virol., 71(1):734-7, (1997), JPN6014045520.

Berendsen, H., "A Glimpse of the Holy Grail?", Science, 282: 642-643, (1998).

Berhanu, A. et al., "Pegloticase Failure and a Possible Solution: Immunosuppression to Prevent Intolerance and Inefficacy in Patients With Gout", Semin Arthritis Rheum., 46(6):754-8, (2017).

Bird et al., "Single-Chain Antigen-Binding Proteins," Science, vol. 242, p. 423-426, Oct. 21, 1988.

Blumberg, B. and Ogston, A., "Further Evidence on the Protein Complexes of Some Hyauronic Acids", Biochem. J. 68:183-188, (1958).

Bossavy, J. et al., "Comparison of the Antithrombotic Effect of PEG-Hirudin and Heparin in a Human Ex Vivo Model of Arterial Thrombosis," Arterioscler. Thromb. Vasc. Biol. 19 :1348-1353, American Heart Association, United States (May 1999).

Bradley, C. and Barrick, D., "Limits of Cooperativity in a Structurally Modular Protein: Response of the Notch Ankyrin Domain to Analogous Alanine Substitutions in Each Repeat," J. Mol. Biol., 324: 373-386, (2002).

Braun, A. and Alsenz, J., "Development and Use of Enzyme-Linked Immunosorbent Assays (ELISA) for the Detection of Protein Aggregates in Interferon-Alpha (IFN-.alpha.) Formulations," Pharm. Res. 14:1394-1400, Plenum Publishing Corporation, United States, (1997).

Braun, A. et al., "Protein Aggregates Seem to Play a Key Role Among the Parameters Influencing the Antigenicity of Interferon Alpha(IFN-.alpha.) in Normal and Transgenic Mice," Pharm. Res. 14:1472-1478, Plenum Publishing Corporation, United States (Oct. 1997).

Brenda Enzyme Database: E.C. 1.7.3.3, Urate Oxidase, available via internet www.brenda-enzymes.info, Mar. 27, 2008; 42 pages.

Buch, M. et al., "Shortening Infusion Times for Infliximab Administration", Rheumatology, vol. 45, pp. 485-486, (2006).

Burnham, N., "Polymers for delivering peptides and proteins," Am. J. Hosp. Pharm. 51: 210-218, American Society of Hospital Pharmacists, Inc., United States, (1994).

Calabrese, L. et al., "Frequency, Distribution and Immunologic Nature of Infusion Reactions in Subjects Receiving Pegloticase for Chronic Refractory Gout", Randomized Controlled Trial., Arthritis Res Ther., 19(1):191, (2017).

Caliceti, P. et al., "Biopharmaceutical Properties of Uricase Conjugated to Neutral and Amphiphilic Polymers", Bioconjugate Chem. 10:639-646, American Chemical Society, (1999).

Carter, W., "Interferon: evidence for subunit structure", PNAS. 67(2), pp. 620-628, (1970).

Chen, R. et al., "Properties of Two Urate Oxidases Modified by the Covalent Attachment of Poly(Ethylene Glycol)," Biochim. Biophys. Acta 660 :293-298, Elsevier/North Holland Biomedical Press, Netherlands, (1981).

Chua, C. et al., "Use of Polyethylene Glycol-Modified Uricase (PEG-Uricase) to Treat Hyperuricemia in a Patient with Non-Hodgkin Lymphoma," Ann. Intern. Med. 109:114-117, American College of Physicians, United States, (1988).

Clark, R. et al., "Long-acting Growth Hormone Produced by Conjugation with Polyethylene Glycol," J. Biol. Chem., 271(36):21969-21977, (1996).

CN Appplication No. 01807750.1; Second Office Action, dated Mar. 21, 2008; 6 pages.

Coiffier, B. et al., "Efficacy and Safety of Rasburicase (recombinant urate oxidase) for the Prevention and Treatment of Hyperuricemia During Induction Chemotherapy of Aggressive Non-Hodgkin's Lymphoma: Results of the GRAAL1 Study", J. Clin. Oncol., 21(23):4402-4406, (2003).

Cole et al., "The EBV-Hybridoma Technique and Its Application to Human Lung Cancer," Monoclonal Antibodies and Cancer Therapy, pp. 77-96, 1985.

Colloc'h, N. et al., "Crystal Structure of the protein drug urate oxidase-inhibitor complex at 2.05 .ANG. resolution," Nature Struct. Biol. 4:947-952, Nature Publishing Group, United Kingdom, (1997).

Conley, T. and Priest, D., "Thermodynamics and Stoicheiometry of the Binding of Substrate Analogues to Uricase," Biochem. J. 187:727-732, The Biochemical Society, United Kingdom, (1980).

Cooper, J., "Resolving LAL Test Interferences", J. Parenter Sci. Technol. 44(1):13-5, (1990).

Cote et al., "Generation of human monoclonal antibodies reactive with cellular antigens," Proc. Natl. Acad.Sci. USA, vol. 80, p. 2026-2030, Apr. 1983.

Crivelli, E. et al., "A Single Step Method for the Solubilization and Refolding of Recombinant Protein from *E. coli* Inclusion Bodies" Australian Journal of Biotechnology vol. 5, No. 2, 78-80, 86 (1991).

Davis, F. et al., "Enzyme-Polyethylene Glycol Adducts: Modified Enzymes with Unique Properties", in Enzyme Engineering, vol. 4, Braun, G. et al., eds, Plenum Press, New York, pp. 169-173, (1978).

Davis. S. et al., "Hypouricaemic Effect of Polyethyleneglycol Modified Urate Oxidase", Lancet, The Lancet Limited, London, GB, pp. 281-283, XP000577404, (1981).

Delgado, C. et al., "The Uses and Properties of PEG-Linked Proteins," Critical Reviews in Therapeutic Drug Carrier Systems, 9(3,4):249-304, (1992).

(56) References Cited

OTHER PUBLICATIONS

Derynck et al., "Expression of human fibroblast interferon gene in *Escherichia coli*," Nature, vol. 287, p. 193-197, Sep. 18, 1980.
Dialog File 351, Accession No. 11389154, Derwent WPI English language abstract for JP 09154581 (Document AO1), dated 1997.
Dialog file 351, Accession No. 8448552, English language abstract for DD 279486 (Document FP3), (2004).
Donadio et al., "Manifestation de Type Anaphylactique apres Injection Intra-Veineuse D'urate-Oxydase Chez Un Enfant Asthmatique Atteint De Leucemie Aigue," La Nouvelle Presse Medicale 10: 711-712 (1981). (English Translation).
EC Number commentary 1.7.3.3 from the Brenda Enzyme Database at <http://www.brenda-enzymes.info> accessed on Mar. 27, 2008.
Embery, G., "Glycosaminoglycans of Human Dental Pulp", J. Biol. Buccale 4:229-236, (1976).
Emmerson, B., "The Management of Gout", N. Engl. J. Med., 334(7):445-451, (1996).
English Language Translation of Brazilian Examination Report dated Oct. 8, 2012 in Brazilian Application No. PI9917760-9, Rio de Janeiro, Brazil.
EP Supplementary Search Report for Application No. 10792756.8 dated Oct. 10, 2013.
Espacenet database, unverified English language abstract for JP 09-154581, Jun. 17, 1997 (Document FP6).
Espacenet Database, Unverified English language abstract of JP 55-099189 A, espacenet.com, European Patent Office (1980).
European Examination Report for European Application No. 01 923 265.1, dated Dec. 13, 2007, European Patent Office, Munich, DE.
European Search Report with Written Opinion dated Oct. 25, 2010, issued in connection with European Patent Application No. 10007912.8.
Examination Report for Application No. 201002407-3 dated Oct. 22, 2013.
Examination Report for Application No. 2604399 dated Nov. 14, 2013.
Examiner's Answer to Appeal Brief mailed on Jul. 11, 2006; in related U.S. Appl. No. 09/839,946, Williams et al., filed Apr. 19, 2001.
ExPasy ProtParam Tool, https://web.expasy.org/cgi-bin/protparam/protparam. Retrieved on Dec. 19, 2018. p. 1-2 (Year: 2018).
Extended European Search Report from European Application No. 14192835.8 dated Jun. 5, 2015.
Extended European Search Report from European Application No. 15156612.2 dated Aug. 14, 2015.
Fam, A., "Strategies and Controversies in the Treatment of Gout and Hyperuricaemia," Bailliere's Clinical Rheumatology: International Practice and Research 4:177-192, Elsevier Science Ltd., (1990).
FDA-Drug Safety Brouchure—Published on the web for Krystexxa, ref ID 3116893 at http://www.accessdata.fda.gov/drugsatfda_docs/label/2012/125293s034lbl.pdf; pp. 1-14, (2012).
Flinta, C. et al., "Sequence Determinants of Cytosolic N-Terminal Protein Processing", Eur J Biochem., 154(1):193-6, (1986).
Forrest, A. et al., "A New Approach for Designing Population Sparse Sampling Strategies—Applied to Ciprofloxacin PKS", Abstracts of Papers, 49(2):153, 1991.
Francis, G. et al., "PEGylation of Cytokines and Other Therapeutic Proteins and Peptides: The Importance of Biological Optimisation of Coupling Techniques", Int J Hematol., 68(1):1-18, (1998).
Freyne, B., "A Case Report of Immunosuppressant Medication-Associated Polyarticular Tophaceous Gout Successfully Treated Using the Polyethylene Glycol-Conjugated Uricase Enzyme Pegloticase", Transplant Proc., 50(10):4099-101, (2018).
Fridovich, I., "The Competitive Inhibition of Uricase by Oxonate and by Related Derivatives of s-Triazines", The Journal of Biological Chemistry, 240:2491-2494, (1965).
Friedman, T. et al., "The urate oxidase gene of *Drosophila pseudoobscura* and *Drosophila malnogaster*: evolutionary changes of sequence and regulation", J Mol. Evol., vol. 34, No. 1, pp. 62-77, (1992). Abstract only.

Fuertges, F. and Abuchowski, A., "The Clinical Efficacy of Poly(Ethylene Glycol)-Modified Proteins," J. Control Release 11:139-148, Elsevier Science, The Netherlands, (1990).
Fujita, T. et al., "Tissue Distribution of 111 In-Labeled Uricase Conjugated with Charged Dextrans and Polyethylene Glycol," J. Pharmacobio-Dyn. 14:623-629, Pharmaceutical Society of Japan, (1991).
Gaertner, H. and Offord, R., "Site-Specific Attachment of Functionalized Poly(ethylene glycol) to the Amino Terminus of Proteins," Bioconjugate Chem. 7:38-44, American Chemical Society, United States (1996).
Ganson, N. et al., "Antibodies to Polyethylene Glycol (PEG) during Phase I Investigation of PEG-Urate Oxidase (PEG-uricase; Puricase. RTM.) for Refractory Gout", presented at American College of Rheumatology Annual Scientific Meeting on Oct. 16-21, 2004 at San Antonio, TX, Poster 808.
Ganson, N., "Control of Hyperuricemia in Subjects with Refractory Gout, and Induction of Antibody Against Poly(ethylene Glycol)(PEG), in a Phase I Trial of Subcutaneous PEGylated Urate Oxidase", Arthritis Research and Therapy, 8(R12):1-10, (2005).
Garay, R. et al., "Antibodies Against Polyeththelene Glycol in Healthy Subjects and in Patients Treated with PEG-Conjugated Agents", Expert Opinion, vol. 9, No. 11, pp. 1319-1323, (2012).
Giglione, C. et al., "Control of Protein life-span by N-terminal methionine excision", EMBO J. vol. 22 No. 1, pp. 13-23, (2003).
Goeddel et al., "Human leukocyte interferon produced by *E. coli* is biologically active," Nature, vol. 287, p. 411, Oct. 2, 1980.
Goldman, S. et al., "A Randomized Comparison Between Rasburicase and Allopurinol in Children with Lymphoma or Leukemia at High Risk for Tumor Lysis", Blood 2001, 97 (10): 2998-3303.
Greenberg, M. and Herschfield, M., "A Radiochemical-High-Performance Liquid Chromatographic Assay for Urate Oxidase in Human Plasma," Anal. Biochem. 176:290-293, Academic Press, Inc., United States, (1989).
Guttmann A etal., Pegloticase in Gout Treatment—Safety Issues, Latest Evidence and Clinical Considerations, Therapeutic Advances in Drug Safety, Dec. 2017;8(12), pp. 379-388.
Hamburger, S. et al., "Arthritis Advisory Committee Meeting. Pegloticase (Krystexxa) IV fusion", dated Jun. 16, 2009 pp. 1-155. [retrieved Aug. 4, 2010]. Available on the internet: <URL: http//www.fda.gov/downloads/AdvisoryCommittees/CommitteesMeetingMaterials/DrugsAdvisoryCommittee/UCM167777.pdf>especially pp. 108-115.
Hamburger, S., et al. Transcript of oral presentation entitled: "Pegloticase (Krystexxatm) IV infusion," pp. 28-213 U.S. Food and Drug Administration, Center for Drug Evaluation and Research, Arthritis Advisory Committee meeting, Jun. 16, 2009.
Hande, K. et at., "Severe Allopurinol Toxicity. Description and Guidelines for Prevention in Patients in Renal Insufficiency," Am. J. Med. 76:47-56, Excerpta Medica, United States, (1984).
Harris, J. et al., Effect of Pegylation on Pharmaceuticals, Nat. Rev. Drug Discov. 2003, 2(3):214-221.
Hartmann, G., "Exchange in vitro of subunits between enzymes from different organisms: chimeras of enzymes", Angew Chem Int Ed Engl., 15(4):181-6, (1976), JPN6014045522.
Hascall, V. and Heinegard, D., "Aggregation of Cartilage Proteoglycans", J. Biol. Chem., 249(13):4232-4241, 4242-4249, and 4250-4256, (1973).
Hazen, J., "Adjuvants—Terminology, Classification, and Chemistry", Weed Technology, vol. 14:773-784, (2000).
Hedlund, L. et al., "Magnetic Resonance Microscopy of Toxic Renal Injury by Bromoethylamine in Rats", Fundamental and Applied Toxicology 16:787-797, Academic Press, (1991).
Heftmann, E. et al., "Chromatography: fundamentals and applications of chromatographic and electrophoretic methods. Part A: fundamentals and techniques." (1983) Journal of Chromatography, vol. 22A, pp. A104-A110.
Heinegard, D. et al., "Characterization of Chondroitin Sulfate Isolated from Trypsin-Chymotrypsin Digests of Cartilage Proteoglycans", Arch. Biochem. Biophys. 165:427-441, (1974).

(56) References Cited

OTHER PUBLICATIONS

Henney, C. and Ellis, E., "Antibody Production to Aggregated Human gamma.G-Globulin in Acquired Hypogammaglobulinemia," New Engl. J. Med. 278:1144-1146, Massachusetts Medical Society, United States (1968).

Herbst, R. et al., "Folding of firefly (*Photinus pyralis*) luciferase: aggreagation and reactivation of unfolding intermediates," Biochemistry, 37 (18) 6586-97, (1998).

Hershfield, M. et al., "Use of Site-Directed Mutagenesis to Enhance the Epitope-shielding Effect of Covalent Modification of Proteins with Polyethylene Glycol", Proc. Natl. Acad. Sci. USA 88:7185-7189, National Academy of Sciences, United States, (1991).

Hershfield, M., "Biochemistry and Immunology of Poly(ethylene glycol)-Modified Adenosine Deaminase (PEG-ADA)," in: ACS Symposium Series 680. Poly(ethylene glycol). Chemsitry and Biological Applications, Harris, J.M. and Zalipsky, S., eds., American Chemical Society, Washington, DC, pp. 145-154 (first available Apr. 1997).

Hinds, K. et al., "Synthesis and Characterization of poly(ethylene glycol)-insuline conjugates," Bioconjugate Chem. 11:195-201, American Chemical Society, United States (Feb. 2000).

Hirel, P. et al., Extent of N-terminal methionine excision from *Escherichia coli* proteins is governed by the side-chain length of the penultimate amino acid, Proc. Natl. Acad. Sci. U.S.A. 86(21): 8247-8251, (1989).

Hortnagl, H. et al., "Membrane Proteins of Chromaffin Granules, Dopamine-hydroxylase, a Major Constituent", The Biochemical Journal, vol. 129, No. 1, pp. 187-195, (1972).

Huse et al., "Generation of a Large Combinatorial Library of the Immunoglobulin Repertoire in Phage Lambda," Science, vol. 246, p. 1275-1281, Dec. 8, 1989.

Huston et al., "Protein engineering of antibody binding sites: Recovery of specific activity in an anti-digoxin single-chain Fv analogue produced in *Escherichia coli*," Proc. Natl. Acad. Sci. USA, vol. 85, pp. 5879-5883, Aug. 1988.

Inada, Y., et al. "Biomedical and biotechnological applications of PEG- and PM-modified proteins," Trends Biotechnol. 13:86-91, Elsevier Science, Ltd., Netherlands (1995).

Information on EC 1.7.3.3—Urate Oxidase: available via internet at www.brenda-enzymes.org/php/flat.sub.--result.php4?ecno=1.7.3.3 &organisms- ub.--list=&Suchword=, Date Jul. 20, 2009.

International Application No. PCT/US1999/017514; International Search Report, dated Mar. 17, 2000; 7 pages.

International Application No. PCT/US1999/017514International Search Report, dated Mar. 17, 2000.

International Application No. PCT/US1999/017678; International Preliminary Report on Patentability, date of completion Aug. 24, 2000; 5 pages.

International Application No. PCT/US1999/017678; International Search Report, dated Feb. 2, 2000; 4 pages.

International Application No. PCT/US2001/040069; International Preliminary Report on Patentabily, date of completeion May 24, 2002; 2 pages.

International Application No. PCT/US2001/040069; International Search Report, dated Dec. 12, 2001; 4 pages.

International Application No. PCT/US2006/013502; International Preliminary Report on Patentability; date of completion Jul. 16, 2007; 05 pages.

International Application No. PCT/US2006/013502; International Search Report and Written Opinion of the International Searching Authority, dated Dec. 13, 2006; 10 pages.

International Application No. PCT/US2006/013660; International Preliminary Report on Patentability, date of completion Mar. 20, 2012; 5 pages.

International Application No. PCT/US2006/013660; International Search Report and Written Opinion of the International Search Authority, dated Nov. 17, 2006; 11 pages.

International Application No. PCT/US2006/013751; International Preliminary Report on Patentability, date of completion Apr. 11, 2005; 5 pages.

International Application No. PCT/US2006/013751; International Search Report and Written Opinion of the International Searching Authority, dated Sep. 6, 2006.

International Application No. PCT/US2010/040082; International Preliminary Report on Patentability, dated Jan. 4, 2012; 6 pages.

International Application No. PCT/US2010/040082; International Search Authority and Written Opinion of the International Search Authority, dated Aug. 19, 2010; 7 pages.

International Application No. PCT/US2010/040093; International Search Report and Written Opinion of the International Searching Authority, dated Aug. 19, 2010; 06 pages.

International Application No. PCT/US2017/061126; International Preliminary Report on Patentability, dated May 23, 2019; 7 pages.

International Application No. PCT/US2017/061126; International Search Report and Written Opinion of the International Searching Authority, dated Feb. 20, 2018; 10 pages.

International Application No. PCT/US2020/015958; International Search Report and Written Opinion of the International Searching Authority, dated Apr. 14, 2020; 14 pages.

International Application No. PCT/US2020/015959; International Search Report and Written Opinion of the International Searching Authority, dated Apr. 8, 2020; 15 pages.

International Preliminary Report on Patentability for PCT/US2010/040082 dated Jan. 4, 2012.

International Search Report for Application No. PCT/US2010/040082 dated Aug. 19, 2010.

Ishino, K. and Kudo, S., "Protein concentration dependence on aggregation behavior and properties of soybean 7S and 11S globulins during alkali-treatment," Agricultural and Biological Chemistry (1980), 44(6), 1259-66.

Ito, M. et al., "Identification of an Amino Acid Residue Involved in the Substrate-binding Site of Rat Liver Uricase by Site-directed Mutagenesis," Biochem. Biophys. Res. Commun. 187:101-107, Academic Press, United States, (1992).

Jaques, L., "The Reaction of Heparin with Proteins and Complex Bases", Biochem. J. 37:189-195, (1943).

Johnson, G. et al., "Reviews of Magnetic Resonance in Medicine", Pergamon, 4:187-219, (1992).

Jones, A., "The Isolation of Bacterial Nucleic Acids using Cetyltrimethylammonium Bromide", Biochim. Biophys. Acta 10:607-612, (1953).

JP Application No. 01-285927; Patent Abstracts of Japan, published Jun. 25, 1991; 1 page.

JP Application No. 19950316359; Patent Abstracts of Japan, published Jun. 17, 1997; 1 page.

JP Application No. 54-005787; Patent Abstracts of Japan, published Jul. 28, 1980; 1 page.

JP Application No. 54-041203; Patent Abstracts of Japan, published Oct. 22, 1980; 1 page.

JP Application No. 56-077153; Patent Abstracts of Japan, published Nov. 26, 1982; 1 page.

JP Application No. 61-093855; Patent Abstracts of Japan, published Mar. 10, 1987; 1 page.

Kabat et al., "Sequences of Proteins of Immunological Interest," US Dept. of Health and Human Services, 1983.

Kahn, K. and Tipton, P., "Kinetic Mechanism and Cofactor Content of Soybean Root Nodule Urate Oxidase," Biochemistry 36:4731-4738, American Chemical Society, United States, (1997).

Kawata, A. et al., "Validation Of The Sf-36 And Haq-Di In Patients With Treatment-Failure Gout", Ann Rheum Dis 2007;66(Suppl II):236, Poster 359.

Kelly, S. et al., "Diabetes Insipidus in Uricase-Deficient Mice: A Model for Evaluating Therapy with Poly(Ethylene Glycol)-Modified Unease," J. Am. Soc. Nephrol. 12:1001-1009, Lippincott Williams & Wilkins, United States, (2001).

Kinsella, J. et al., "Uricase From Fish Liver: Isolation and Some Properties", Comp Biochem Physiol B., 82(4):621-4, (1985).

Kinstler, O. et al., "Characterization and Stability of N-terminally PEGylated rhG-CSF," Pharm. Res. 13:996-1002, Plenum Publishing Corporation, United States (1996).

Kissel P. et al., "Modification of Uricaemia and the Excretion of Uric Acid Nitrogen by an Enzyme of Fungal Origin", Nature 1968, 217: 72-74.

(56) References Cited

OTHER PUBLICATIONS

Kito, M. et al., "A Simple and Efficient Method for Preparation of Monomethoxypolyethylene Glycol Activated with p-Nitrophenylchloroformate and Its Application to Modification of L-Asparaginase," J. Clin. Biochem. Nutr. 21:101-111, Institute of Applied Biochemistry, Japan (1996).
Kohler et al., "Continuous cultures of fused cells secreting antibody of predefined specificity," Nature, vol. 256, p. 495-497, Aug. 7, 1975.
Kontsek,P. et al., "Forty years of interferon," Acta Virologica 41:349-353, Slovak Academic Press, Slovak Republic, (1997).
Kozbor et al., "The production of monoclonal antibodies from human lymphocytes," Immunology Today, vol. 4, No. 3, p. 72, 1983.
Kozma, E. et al., "An Accumulation of Proteoglycans in Scarred Fascia", Mol. Cell. Biochem. 203:103-12, (2000).
Kral, L. et al, "Cloning a cDNA for *Drosophila melanogaster* urate oxidase," Gene 45:131-137, Elsevier Science Publishers B.V., Netherlands (1986).
Kunitani, M. et al., "Classical light scattering quantitation of protein aggregates: off-line spectroscopy versus HPLC detection," J. Pharm. Biomed. Anal. 16:573-586, Elsevier Science B.V., Netherlands (Dec. 1997).
Kunitani, M. et al., "On-Line Characterization of Polyethylene Glycol-Modified Proteins," Journal of Chromatography 588:125-137, Elsevier Science Ltd. (1991).
Larsen, K. "Purification of Nodule-Specific Uricase from Soybean by Arginine-Sepharose Affinity Chromatography", Prep Biochem. 1990; 20(1):1-9 (Abstract Only).
Laurent, T. et al., "Fractionation of Hyaluronic Acid: The Polydispersity of Hyaluronic Acid from the Bovine Vitreous Body", Biochem. Biophys. Acta 42:476-485, (1960).
Lawrence, R. et al., "Estimates of the Prevalence of Arthritis and Selected Musculoskeletal Disorders in the United States", Arthritis Rheum., 41(5):778-99, (1998).
Leach, M. et al., "Efficacy of Urate Oxidase (Uricozyme) in Tumor Lysis Induced Urate Nephropathy", Clin Lab Haematol 20:169-172, Blackwell Science Limited (Jun. 1998).
Leaustic M. et al., 1983, Rev. Rhum. Mal. Osteoartic 50:553-554.
Lee, C. et al., "Generation of cDNA Probes Directed by Amino Acid Sequence: Cloning of Urate Oxidase," Science 239:1288-1291, American Association for the Advancement of Science, United States, (1988).
Lee, S., "Studies on Glycosaminoglycans in Tissues", Fukushima J. Med. Sci. 19:33-39, (1973).
Lee, T. et al., "A Novel Secretory Tumor Necrosis Factor-Inducible Protein (TSG-6) Is a Member of the Family of Hyaluronate Binding Proteins, Closely Related to the Sdhesion ReceptorCD44", J. Cell Biol., 116(2): 545-557, (1992).
Legoux, R. et al., "Cloning and Expression in *Eschericia coli* of the Gene Encoding *Aspergillus flavus* Urate Oxidase", J. Biol. Chem. 267:8565-8570, American Society for Biochemistry and Molecular Biology, United States, (1992).
Li-Yu, J. et al., "Mutations at the S1 Sites of methionine Aminopeptidases from *Escherichia coli* and *Homo sapiens* Reveal the residues Critical for Substrate Specificity", J. Biol. Chem. 279(20): 21128-21134, (2004).
Li-Yu, J. et al., "Treatment of Chronic Gout. Can We Determine When Urate Stores Are Depleted Enough to Prevent Attacks of Gout?" J. Rheumatol 2001, 28(3):577-580.
Lim, S. et al., "Trends in Gout and Rheumatoid Arthritis Hospitalizations in the United States, 1993-2011", JAMA, 315(21):2345-7, (2016).
Lipsky, P. et al., "Pegloticase Immunogenicity: The Relationship Between Efficacy and Antibody Development in Patients Treated for Refractory Chronic Gout", Arthritis Res Ther., 16(2):R60, (2014).
List of Gen Bank Accession Nos. for Uricase Family Member Sequences submitted by Applicants in corresponding South Korean National Phase Application 10-2007-7025066 of International Application PCT/US2006/013751 (2004).
Liu, C. et al., "Prednisone in Uric Acid Lowering in Symptomatic Heart Failure Patients with Hyperuricemia (PUSH-PATH) Study", Can J Cardiol., 29(9):1048-54, (2013).
London, M. et al., "Uricolytic Activity of Purified Uricase in Two Human Beings", Science 1957, 125:937-938.
Macart et al., "An improvement of the Coomassie Blue dye binding method allowing an equal sensitivity to various proteins: application to cerebrospinal fluid," Clinica Chimica Acta, 122 (1982) 93-101, Elsevier Biomedical Press.
Maccari, F. and Volpi, N., "Glycosaminoglycan blotting on nitro-cellulose membranes treated with cetylpyridinium chloride after agarose-gel electrophoretic separation", Electrophoresis 23:3270-3277, (2002).
Mahler, H. et al., "Studies of Uricase. 1. Preparation, Purification, and Properties of a Cuproprotein," J. Biol. Chem. 216:625-641, American Society for Biochemistry and Molecular Biology, United States (1955).
Mahmoud, H. et al., "Advances in the Management of Malignancy-Associated Hyperuricaemia", Br. J. Cancer (Supplement 4) 77:18-20, Churchill Livingstone, United Kingdom, (1998).
Malakhova, E. et al., "Kinetic properties of bacterial urate oxidase entrapped in hydrated reversed micelles," (1991), Biologicheskie Membrany 8(5), 453-9 (abstract only).
Matsumura, G. et al., "The Preparation of Hyaluronic Acid from Bovine Synovial Fluid", Biochim. Biophys. Acta 69:574-576, (1963).
Miura, S. et al., "Urate Oxidase is Imported into Peroxisomes Recognizing the C-terminal SKL Motif of Proteins," Eur. J. Biochem. 223:141-146, Blackwell Science Ltd., United Kingdom, (1994).
Moerschell, R. et al., The Specificities of Yeast Methionine Aminopeptidase and Acetylation of Amino-terminal Methionine in Vivo, J. Biol. Chem. 265: 19638-19643, (1990).
Monkarsh, S. et al., "Positional isomers of monopegylated interferon alpha-2a: isolation, characterization, and biological activity," Anal. Biochem. 247:434-440, Academic Press, United States, (1997).
Montagnac, R. and Schillinter, F., Letter to Editor, Nephrologie, 11 (4):259, (1990).
Montalbini, P. et al., "Isolation and characterization of uricase from bean leaves and its comparison with uredospore enzymes," Plant Sci. 147:139-147, Elsevier Science Ireland Ltd., Ireland (Sep. 1999).
Montalbini, P. et al., "Uricase from leaves: its purification and characterization from three different higher plants," Planta 202:277-283, Springer-Verlag, Germany (Jul. 1997).
Moolenburgh, J.D. et al., "Rasburicase treatment in severe tophaceous gout: a novel therapeutic option." (2006) Clin. Rheumatol., vol. 25, pp. 749-752.
Moore, W. and Leppert, P., "Role of Aggregated Human Growth Hormone (hGH) in Development of Antibodies to hGH," J. Clin. Endocrinol. Metab. 51:691-697, The Endocrine Society, United States, (1980).
Morrison et al., "Chimeric human antibody molecules: Mouse antigen-binding domains with human constant-region domains," Proc. Natl. Acad. Sci. USA, vol. 81, pp. 6851-6855, Nov. 1984.
Motojima et al., "Cloning and sequence analysis ofcDNA for rat liver uricase," JBC 263(32):16677-81, (1988).
Mourad, G. et al., "Role of Anti-Urate Oxidase Precipitant Antibodies in Urate Oxidase Resistant Hyperuremic", La Presse Medicale, 13 (42):2585, (1984).
Moussy, G. et al., "Inter-species DNA polymerase delta chimeras are functional in *Saccharomyces cerevisiae* ", Eur J Biochem., 231(1):45-9, (1995), JPN6014045517.
Nagata et al., "Synthesis in *E. coli* of a polypeptide with human leukocyte interferon activity," Nature, vol. 284, p. 316, Mar. 27, 1980.
Nahm, B. et al., "Induction and De Novo Synthesis of Uricase, a Nitrogen-Regulated Enzyme in Neurospora Crassa," J Bacteriol., 169(5):1943-8, (1987).
NCBI Entrez Protein (PRF) Database, deposited sequence for rat urate oxidase (NP 446220), Wang, X.D., et al., National Lirary of

(56) References Cited

OTHER PUBLICATIONS

Medicine, National institutes of Health, Accession No. 20127395, accessed at http://www.ncbi.nlm.nih.gov/protein/20127395, accessed on Dec. 10, 2003.
Neuberger et al., "Recombinant antibodies possessing novel effector functions," Nature, vol. 312, p. 604-608, Dec. 13, 1984.
Ngo, J. et al., "Computational Complexity, Protein Structure Prediction, and the Levinthal Paradox", The Protein Folding Problem and Tertiary Structure Prediction, K. Merc Jr. and S. Le Grand Edition, pp. 491-495, (1994).
Nishida, Y. et al., "Hypouricaemic effect after oral administration in chickens of polyethylene glycol-modified uricase entrapped in liposomes", J. Pharm. Pharmacol. 36:354-355, Pharmaceutical Press, United Kingdom, (1984).
Nishimura, H. et al., "Improved Modification of Yeast Uricase with Polyethylene Glycol: Accompanied with Nonimmunoreactivity Towards Anti-Uricase Serum and High Enzymic Activity", Enzyme 26:49-53, Karger, Switzerland, (1981).
Nishimura, H. et al., "Modification of Yeast Uricase with Polyethylene Glycol: Disappearance of Binding Ability towards Anti-Uricase Serum", Enzyme 24:261-264, Karger, Switzerland, (1979).
Nucci, M. et al., "The Therapeutic Value of Poly(Ethylene Glycol)-Modified Proteins", Adv. Drug Deliv. Rev. 6:133-151, Elsevier Science Publishers, Netherlands, (1991).
Osman, A. et al., "Liver uricase in Camelus dromedarius: purification and properties", Comparative Biochemistry and Physiology. B. Comparative Biochemistry, Pergamon Press, London, GB, (1989), vol. 94B, No. 3, ISSN 0305-0491, pp. 469-474, XP002125210.
Otta, M. and Bertini, F., "Solubilization of Particle-Linked Urate Oxidase by Different Agents", Acta Physiol. Latinoam, 25:451-457, (1975).
Pakula, A. et al., "Genetic Analysis of Protein Stability and Function", Annu Rev Genet., 23:289-310, (1989).
Palleroni, A. et al., "Interferon Immunogenicity: Preclinical Evaluation of Interferon-.alpha.2a," J. Interferon Cyto. Res. 17:S23-S27, Mary Ann Liebert, Inc., United States, (1997).
Patent Abstract of Japan, English language abstract of JP 03-148298, Japanese Patent Office (1980).
Patent Abstracts of Japan, (Dec. 5, 2003), vol. 2003, No. 12.
Patton, J., "Mechanisms of Macromolecule Absorption by the Lungs", Adv. Drug Delivery Rev., 19(1):3-36, (1996).
PCR Technology. Principles and Applications for DNA Amplification, Stockton Press, (1989).
Pearce, R. and Mathieson, J., "Quantitative Isolation of Purified Acidic Glycosaminoglycans from Rat Skin", Can. J. Biochemistry 45:1565-1576, (1967).
Perez-Ruiz, F. et al., "Effect of Urate-Lowering Therapy on the Velocity of Size Reduction of Tophi in Chronic Gout", Arthritis Rheum. 2002, 47(4); 356-360.
Philippovich, Y., "The Fundamentals of Biochemistry", AGAR: 29-30, (1999) (Partial English translation).
Pitts, O. et al., "Uricase: Subunit Composition and Resistance to Denaturants", Biochemistry, 13(5):888-92, (1974).
Porstmann, B. et al., "Comparison of Chromogens for the Determination of Horseradish Peroxidase as a Marker in Enzyme Immunoassay," J. Clin. Chem. Clin. Biochem. 19:435-439, Walter de Gruyter & Co., Germany, (1981).
Potaux, L. et al., "Uricolytic Therapy Value of Urate Oxidase in the Treatment of Hyperuricemia", Nouv. Presse Med., 1975, 4:1109-1112.
Prevent—definition by Merriam-Webster online dictionary; at the web http://www.merriam-webster.com/dictionary/prevent-pages 1-3, accessed on Jun. 27, 2013.
Pui, C. et al., "Urate oxidase in prevention and treatment of hyperuricemia associated with lymphoid malignancies," Leukemia 11:1813-1816, Stockon Press, United States, (1997).
R&D Focus Drug News (DataStar File IPNR/IPNA), Accession No. 1998:2984 DRUGNL, "PEG-uricase BioTechnology General, Duke University, Mountain View licensing agreement," (Aug. 24, 1998).

Reinders, M., "Practice Research in the Field of Gout: Clinical Pharmacology of Antihyperuricemic Drugs", University of Groningen, Doctoral Thesis, 152 pages; p. 18, table 2; p. 131, paragraph 2; (2008).
Remington's Pharmaceutical Sciences, Mack Publishing Co., (1990).
Richette, P. et al., "Rasburicase for Tophaceous Gout not Treatable with Allopurinol: An Exploratory Study", Rheumatol., 34(10):2093-8, (2007).
Richette, P. et al., "Successful Treatment with Rasburicase of a Tophaceous Gout in a Patient Allergic to Allopurinol", Nature Clinical Practice Rheumatology, 2(6):338-342, (2006).
Rinella, J. et al., "Elutability of Proteins from Aluminum-Containing Vaccine Adjuvants by Treatment with Surfactants", J. Colloid Interface Sci. 1998;197:48-56. (1998).
Rosenberg, A., "Effects of Protein Aggregates: An Immunologic Perspective", AAPS J., 8(3):E501-7, (2006).
Rozenberg, S. et al., "Urate-Oxidase for the Treatment of Tophaceous Gout in Heart Transplant Recipients", Rev Rhum, vol. 62 (5), Eng. Ed. pp. 392-394, (1995).
Rudinger, J., "Characteristics of the amino acids as components of a peptide hormone sequence," Peptide Hormones, JA Parsons Edition, University Park Press, Jun. 1976, pp. 1-7.
Saag K., et al., FRI0240 Clinical trial to determine whether altering the regimen of pegloticase administration can increase the frequency of subjects having sustained lowering of serum urate, Annals of Rheumatic Disease, Friday, Jun. 15, 2018, vol. 77, pp. 661.
Saifer, M. et al., "Improved Conjugation of Cytokines Using High Molecular Weight Poly(ethylene glycol): PEG-GM-CSF as a Prototype," Polymer. Prepr. 38:575-577, American Chemical Society, United States, (1997).
Saifer, M. et al., "Plasma clearance and immunologic properties of long-acting superoxide dismutase prepared using 35,000 to 120,000 dalton poly-ethylene glycol," Adv Exp Med Biol (1994) 366: 377-387.
Saito, S., "Coagulation and Peptization of Polyelectrolyte Solution by Detergent Ions. I", Kolloid-Zeitschrift 143(2):66-73, (1955).
Sakane, T. and Pardridge, W., "Carboxyl-directed Pegylation of Brain-derived Neurotrophic Factor Markedly Reduces Systemic Clearance with Minimal Loss of Biologic Activity", Pharm. Res. 14:1085-1091, Plenum Publishing Corporation, United States, (1997).
Sambrook, J. et al., "Molecular Cloning. A Laboratory Manual", Cold Spring Harbor Laboratory Press, (1989).
Sartore, L. et al., "Enzyme Modification by mPEG with an Amino Acid or Peptide as Spacer Arms", Applied Biochemistry and Biotechnology 27: 55-63, (1991).
Savoca, K. et al., "Induction of Tolerance in Mice by Uricase and Monomethoxypolyethylene Glycol-Modified Uricase," Int. Archs. Allergy Appl. Immun. 75:58-67, Karger, (1984).
Scandella et al., "A Membrane-Bound Phospholipase Al Purified from *Escherichia colt*," Biochemistry, vol. 10, No. 24, p. 4447, 1971.
Schiavon, O. et al., "Therapeutic proteins: a comparison of chemical and biological properties of uricase conjugated to linear or branched poly(ethylene glycol) and poly(N-acryloylmorpholine)", II Farmaco, 55(4):264-9, (2000).
Schinzel, R. et al., "The phosphate recognition site of *Escherichia coli* maltodextrin phosphorylase," FEBS, Jul. 1991, 286(1, 2): 125-128.
Schumacher, H. et al., "Outcome Evaluations in Gout", J Rheumatol., 34(6):1381-5, (2007), XP008158539.
Schumacher, R. et al., "Effects of Febuxostat Versus Allopurinol and Placebo in Reducing Serum Urate in Subjects with Hyperuricemia and Gout: A 28-Week, Phase III, Randomized, Double-Blind, Parallel-Group Trial", Arthritis & Rheumatism (Arthritis Care & Research), vol. 59, No. 11, pp. 1540-1548, (2008).
Scott, J., "Aliphatic Ammonium Salts in the Assay of Acidic Polysaccharides from Tissues", Methods Biochem. Anal. 8:145-197, (1960).
Scott, J., "The Precipitation of Polyanions by Long-Chain Aliphatic Ammonium Salts", Biochem. J. 81:418-424, (1961).

(56) References Cited

OTHER PUBLICATIONS

Scott, J., "The Reaction of Long-Chain Quarternary Ammonium Salts with Acidic Polysaccharides", Chem. and Ind., 168-169, (1955).
Scott, J., "The solubility of cetylpyridinium complexes of biological polyanions in solution of salts", Biochim, Biophys. Ada 18:428-429, (1955).
Search Report for Application No. 201102592-1, dated Jul. 6, 2012.
Seng Yue, C. et al., Population Pharmacokinetic and Pharmacodynamic Analysis of PEG-uricase in Subjects With Hyperuricemia and Refractory Gout, presented at the American College of Clinical Pharmacy 2006 Annual Meeting on Oct. 26-29, 2006 at St. Louis, Missouri, Poster.
Serafini-Fracassini, A. et al., "The Protein-Polysaccharide Complex of Bovine Nasal Cartilage", Biochem. J. 105:569-575, (1967).
SG Application No. 201102592-1; Invitation to Respond to Written Opinion, dated Nov. 21, 2013; 8 pages.
Sharma, B., "Immunogenicity of Therapeutic Proteins. Part 3: Impact of Manufacturing Changes", Biotech Adv., 25(3):325-31, (2007).
Shearwater Polymers Inc., "Functionalized Biocompatible Polymers for Research and Pharmaceuticals," in Shearwater Polymers, Inc., Catalog, pp. 27, 47, and 48, (1997).
Sherman, F. et al., "Methionine or not methionine at the beginning of a protein", Bio Essays, vol. 3, Issue 1, pp. 27-31, (1985).
Sherman, M. et al., "Conjugation of High-Molecular Weight Poly-(ethylene glycol) to Cytokines: Granulocyte-Macrophage Colony-Stimulating Factors as Model Substrates", ACS Symposium Series 680. Poly(ethylene glycol). Chemistry and Biological Applications, Harris, J.M. and Zalipsky, S., eds., American Chemical Society, Washington, DC, pp. 155-169, (1997).
Sherman, M. et al., "PEG-Uricase in the Management of Treatment-Resistant Gout and Hyperuricemia", Advanced Drug Delivery Reviews, 60(1):59-68, (2008).
Shoji, A. et al., A Retrospective Study of the Relationship Between Serum Urate Level and Recurrent Attacks of Gouty Arthritis: Evidence for Reduction of Recurrent Gouty Arthritis With Antihyperuricemic Therapy, Arthritis Rheum., 51(3):321-325, (2007).
Sigma Catalog, p. 1008, Product Nos. U 3250, 292-8, U3500, U 9375 or U 3377, (1993).
Singapore Search Report for Application No. 201109356-4, dated Feb. 15, 2013.
Smith, T. et al., "Human Lung Tryptase", J. Biol. Chem., 259(17):11046-11051, (1984).
Somack, R. et al., "Preparation of Long-Acting Superoxide Dismutase Using High Molecular Weight Polyethylene Glycol (41,000-72,000 Daltons)", Free Rad. Res. Comms. 12-13:553-562, Harwood Academic Publishers GmBH, Germany, (1991).
Sorensen LB, Suppression of the Shunt Pathway in Primary Gout by Azathioprine, Proceedings of the National Academy of Science of the USA, Mar. 1966;55(3) pp. 571-575.
Streuli et al., "Target cell specificity of two species of human interferon-a produced in*Escherichia coli* and of hybrid molecules derived from them," Proc. Natl. Acad. Sci. USA, vol. 85, pp. 5879-5883, Aug. 1988.
Sundy, J. and Hershfield, M., "Uricase And Other Novel Agents For The Management Of Patients With Treatment-Failure Gout", Curr Rheumatol Rep. Jun. 2007; 9(3):258-64.
Sundy, J. et al., "A Phase I Study of Pegylated-Uricase (Puricase. RTM.) in Subjects with Gout", presented at American College of Rheumatology Annual Scientific Meeting on Oct. 16-21, 2004 at San Antonio, TX, Poster 807.
Sundy, J. et al., "Efficacy and Tolerability of Pegloticase for the Treatment of Chronic Gout in Patients Refractory to Conventional Treatment: Two Randomized Controlled Trials", American Medical Association, 306(7):711-20, (2011).
Sundy, J. et al., "Pharmacokinetics and Pharmacodynamics of Intravenous PEGylated Recombinant Mammalian Urate Oxidase in Patients With Refractory Gout", Arth Rheum., 56(3):1021-8, (2007).
Sundy, J. et al., "Reduction of Plasma Urate Levels Following Treatment with Multiple Doses of Pegloticase in Patients with Treatment-Failure Gout", Arthritis Rheum., 58(9):2882-91, (2008).
Sundy, J. et al., "A Phase 1 Study of Pegylated-Uricase (Puricase) in Subjects with Gout", Arthritis Rheum. 2004 vol. 50, supplement 9, S337-338.
Sundy, J. et al., "A Phase 2 Study of Multiple Doses of Intravenous Polyethylene Glycol (PEG)-uricase in Patients with Hyperuricemia and Refractory Gout", presented at American College of Rheumatology 2005 Annual Scientific Meeting on Nov. 12-17, 2005 at San Diego, CA, #1836.
Sundy, J. et al., "A Phase 2 Study of Multiple Doses of Intravenous Polyethylene Glycol (PEG)-uricase in Patients with Hyperuricemia and Refractory Gout", presented at the EULAR—Annual European Congress of Rheumatology, on Jun. 21-24, 2006 at Amsterdam, Netherlands, Poster 516.
Sundy, J. et al., "Quality of Life in Patients With Treatment-Failure Gout", presented at the EULAR—Annual European Congress of Rheumatology, on Jun. 21-24, 2006 at Amsterdam, Netherlands, Poster 517.
Sundy, J. et al., A Multicenter Longitudinal Study of Disease Characteristics in Patients With Treatment-Failure Gout, presented at the EULAR—Annual European Congress of Rheumatology, on Jun. 21-24, 2006 at Amsterdam, Netherlands, Poster 518.
Surina, T. et al., "Urate Oxidase From Pig Liver: Biochemical and Immunological Properties", Prikl Biokhim Mikrobiol., 14(4):533-42, (1978).
Sütterlin, H. et al., "Mixtures of Quaternary Ammonium Compounds and Anionic Organic Compounds in the Aquatic environment: Elimination and Biodegradability in the Closed Bottle Test Monitored by LC-MS/MS", Chemosphere, 72(3):479-84, (2008), (Abstract only).
Suzuki, H. et al., "Soybean Nodule-Specific Uricase (Nodulin-35) Is Expressed and Assembled into a Functional Tetrameric Holoenzyme in *Escherichia coli*", Plant Physiol., 95(2):384-9, (1991).
Takeda et al., "Construction of chimaeric processed immunoglobulin genes containing mouse variable and human constant region sequences," Nature, vol. 314, p. 452-454, Apr. 4, 1985.
Terkeltaub, R., "Clinical Practice. Gout", N Engl J Med., 349(17):1647-55, (2003).
Tomanee, P. et al., "Fractionation of Protein, RNA, and Plasmid DNA in Centrifugal Precipitation Chromatography Using Cationic Surfactant CTAB Containing Inorganic Salts NaCl and NH(4)Cl", Biotechnol Bioeng., 88(1):52-9, (2004).
Tomohiro, JP 2005-241424 (Sep. 8, 2005) English language mechanical translation provided.
Treuheit, M. et al., "Inverse Relationship of Protein Concentration and Aggregation", Pharm Res., 19(4):511-6, (2002).
Truscoe, R. et al., "Effect of pH on Extraction and Activity of Ox-Kidney Urate Oxidase", Biochim Biophys Acta., 89:179-82, (1964).
Truscoe, R., "Effect of Detergents on Extraction and Activity of Ox-Kidney Urate Oxidase", Enzymologia, 33(1):119-32, (1967).
Tsuji, J. et al., "Studies on Antigenicity of the Polyethylene Glycol (PEG)-Modified Uriacse", Int J Immunopharmacol., 7(5):725-30, (1985).
Tsunasawa, S. et al., "Amino-terminal Processing of Mutant Forms of Yeast iso-1-cytochrome C. The Specificities of Methionine Aminopeptidase and Acetyltransferase", J Biol Chem., 260(9):5382-91, (1985).
U.S. Appl. No. 09/370,084; Notice of Allowability dated Jan. 13, 2003.
U.S. Appl. No. 09/370,084; Office Action dated Mar. 21, 2001.
U.S. Appl. No. 09/370,084; Office Action dated May 29, 2002.
U.S. Appl. No. 09/370,084; Office Action dated Sep. 13, 2002.
U.S. Appl. No. 09/501,730; Advisory Action dated Nov. 17, 2003; 5 pages.
U.S. Appl. No. 09/501,730; Declaration of Merry R. Sherman, Ph.D. Under 37 C.F.R. Section 1.132 dated Sep. 20, 2002; 5 pages.
U.S. Appl. No. 09/501,730; Final Office Action dated May 22, 2002; 8 pages.
U.S. Appl. No. 09/501,730; Final Office Action dated Feb. 10, 2004; 8 pages.

(56) References Cited

OTHER PUBLICATIONS

U.S. Appl. No. 09/501,730; Final Office Action dated Jun. 18, 2003; 9 pages.
U.S. Appl. No. 09/501,730; Non-Final Office Action dated Apr. 6, 2001; 12 pages.
U.S. Appl. No. 09/501,730; Non-Final Office Action dated Dec. 3, 2002; 11 pages.
U.S. Appl. No. 09/501,730; Non-Final Office Action dated Dec. 5, 2001; 9 pages.
U.S. Appl. No. 09/501,730; Notice of Allowance dated Feb. 24, 2004; 6 pages.
U.S. Appl. No. 09/501,730; Notice of Allowance dated Jan. 13, 2004; 8 pages.
U.S. Appl. No. 09/501,730; Notice of Appeal dated Sep. 9, 2003; 1 page.
U.S. Appl. No. 09/501,730; Petition Decision mailed on Jul. 12, 2007.
U.S. Appl. No. 09/501,730; Supplemental Notice of Allowability dated Feb. 24, 2004.
U.S. Appl. No. 09/762,097; Final Office Action dated Aug. 1, 2005; 5 pages.
U.S. Appl. No. 09/762,097.
U.S. Appl. No. 09/762,097; Non-Final Office Action dated Mar. 16, 2005; 6 pages.
U.S. Appl. No. 09/762,097; Non-Final Office Action dated Oct. 15, 2002; 8 pages.
U.S. Appl. No. 09/762,097; Non-Final Office Action dated Oct. 24, 2003; 6 pages.
U.S. Appl. No. 09/762,097; Notice of Allowance dated Nov. 21, 2005; 5 pages.
U.S. Appl. No. 09/839,946; Advisory Action, dated Dec. 5, 2005; 9 pages.
U.S. Appl. No. 09/839,946; BPAI Decision, decided on Jul. 18, 2007; 7 pages.
U.S. Appl. No. 09/839,946; Declaration of Merry R, Sherman Under 37 C.F.R. Section 1,132 dated May 26, 2005; 8 pages.
U.S. Appl. No. 09/839,946; Declaration of Merry R, Sherman Under 37 C.F.R. Section 1,132 dated Sep. 18, 2007; 19 pages.
U.S. Appl. No. 09/839,946; Final Office Action dated Jan. 2, 2009; 8 pages.
U.S. Appl. No. 09/839,946; Final Office Action dated Oct. 16, 2009; 8 pages.
U.S. Appl. No. 09/839,946; Final Office Action, dated Jul. 20, 2005; 14 pages.
U.S. Appl. No. 09/839,946; Final Office Action, dated Mar. 5, 2004; 9 pages.
U.S. Appl. No. 09/839,946; Non-Final Office Action, dated Jan. 26, 2005; 12 pages.
U.S. Appl. No. 09/839,946; Non-Final Office Action dated Aug. 11, 2008; 6 pages.
U.S. Appl. No. 09/839,946; Non-Final Office Action dated Jul. 23, 2008; 7 pages.
U.S. Appl. No. 09/839,946; Non-Final Office Action dated May 11, 2009; 8 pages.
U.S. Appl. No. 09/839,946; Non-Final Office Action, dated Sep. 11, 2003; 12 pages.
U.S. Appl. No. 09/839,946; Non-Final Office Action, dated Aug. 2, 2004; 7 pages.
U.S. Appl. No. 09/839,946; Notice of Allowability dated Dec. 23, 2009; 5 pages.
U.S. Appl. No. 09/839,946; Notice of Appeal dated Dec. 20, 2005; 1 page.
U.S. Appl. No. 09/839,946; Notice of Hearing mailed May 15, 2007; 1 page.
U.S. Appl. No. 10/928,370; Final Office Action dated Dec. 30, 2011; 10 pages.
U.S. Appl. No. 10/928,370; Final Office Action dated Aug. 5, 2010; 8 pages.
U.S. Appl. No. 10/928,370; Final Office Action dated Jun. 22, 2009;11 pages.
U.S. Appl. No. 10/928,370; Final Office Action dated Nov. 2, 2007; 15 pages.
U.S. Appl. No. 10/928,370; Non-Final Office Action dated Jun. 9, 2011; 14 pages.
U.S. Appl. No. 10/928,370; Non-Final Office Action dated Mar. 18, 2014; 9 pages.
U.S. Appl. No. 10/928,370; Non-Final Office Action dated Apr. 9, 2007; 14 pages.
U.S. Appl. No. 10/928,370; Non-Final Office Action dated Dec. 9, 2009; 11 pages.
U.S. Appl. No. 10/928,370; Non-Final Office Action dated Sep. 30, 2008; 9 pages.
U.S. Appl. No. 10/928,370; Notice of Appeal dated May 1, 2008; 1 page.
U.S. Appl. No. 11/357,028; Advisory Action dated Dec. 20, 2012; 4 pages.
U.S. Appl. No. 11/357,028; Advisory Action dated Jan. 15, 2008; 3 pages.
U.S. Appl. No. 11/357,028; Advisory Action dated Mar. 16, 2010; 3 pages.
U.S. Appl. No. 11/357,028; Advisory Action dated Mar. 18, 2009; 4 pages.
U.S. Appl. No. 11/357,028; Applicant Initiated Interview Summary dated Aug. 13, 2012; 3 pages.
U.S. Appl. No. 11/357,028; Applicant Initiated Interview Summary dated Feb. 12, 2013; 3 pages.
U.S. Appl. No. 11/357,028; Final Office Action dated Aug. 27, 2007; 11 pages.
U.S. Appl. No. 11/357,028; Final Office Action dated Dec. 31, 2008; 13 pages.
U.S. Appl. No. 11/357,028; Final Office Action dated Jan. 4, 2010; 14 pages.
U.S. Appl. No. 11/357,028; Final Office Action dated Jun. 8, 2012; 14 pages.
U.S. Appl. No. 11/357,028; Final Office Action dated Jun. 13, 2011; 8 pages.
U.S. Appl. No. 11/357,028; Non-Final Office Action dated Dec. 6, 2011; 13 pages.
U.S. Appl. No. 11/357,028; Non-Final Office Action dated Feb. 7, 2007; 9 pages.
U.S. Appl. No. 11/357,028; Non-Final Office Action dated Jul. 5, 2016; 4 pages.
U.S. Appl. No. 11/357,028; Non-Final Office Action dated Jul. 12, 2013; 9 pages.
U.S. Appl. No. 11/357,028; Non-Final Office Action dated Mar. 25, 2008; 10 pages.
U.S. Appl. No. 11/357,028; Non-Final Office Action dated May 29, 2009; 16 pages.
U.S. Appl. No. 11/357,028; Non-Final Office Action dated Oct. 13, 2010; 10 pages.
U.S. Appl. No. 11/357,028; Notice of Appeal dated Apr. 5, 2010; 1 page.
U.S. Appl. No. 11/357,028; Notice of Appeal dated Dec. 10, 2012; 1 page.
U.S. Appl. No. 11/539,475; Final Office Action dated Apr. 28, 2011; 9 pages.
U.S. Appl. No. 11/539,475; Final Office Action dated Oct. 30, 2009; 2 pages.
U.S. Appl. No. 11/539,475; Final Office Action, dated Oct. 30, 2009; 6 pages.
U.S. Appl. No. 11/539,475; Non-Final Office Action dated Sep. 9, 2010; 7 pages.
U.S. Appl. No. 11/539,475; Non-Final Office Action, dated Jun. 25, 2009; 6 pages.
U.S. Appl. No. 11/539,475; Notice of Allowance dated Oct. 19, 2011; 5 pages.
U.S. Appl. No. 11/833,590; Notice of Allowance dated Dec. 1, 2010; 9 pages.
U.S. Appl. No. 11/833,590; Office Action dated Mar. 22, 2010; 10 pages.
U.S. Appl. No. 11/882,750; Non-Final Office Action dated Mar. 17, 2010; 9 pages.

(56) References Cited

OTHER PUBLICATIONS

U.S. Appl. No. 11/882,750; Notice of Allowance dated Dec. 14, 2010; 6 pages.
U.S. Appl. No. 11/899,688; Final Office Action dated Jun. 24, 2010; 7 pages.
U.S. Appl. No. 11/899,688; Final Office Action dated Oct. 24, 2011; 5 pages.
U.S. Appl. No. 11/899,688; Non-Final Office Action dated May 6, 2011; 7 pages.
U.S. Appl. No. 11/899,688; Non-Final Office Action, dated Oct. 30, 2009; 10 pages.
U.S. Appl. No. 11/918,292; Advisory Action dated Feb. 8, 2012; 3 pages.
U.S. Appl. No. 11/918,292; Applicant Initiated Interview Summary dated Jun. 13, 2016; 4 pages.
U.S. Appl. No. 11/918,292; Declaration of Meir Fischer Under 37 C.F.R Section 1.132 dated Aug. 17, 2011; 3 pages.
U.S. Appl. No. 11/918,292; Final Office Action dated Feb. 5, 2015; 10 pages.
U.S. Appl. No. 11/918,292; Final Office Action dated Nov. 3, 2011; 10 pages.
U.S. Appl. No. 11/918,292; Non-Final Office Action dated Feb. 17, 2011; 10 pages.
U.S. Appl. No. 11/918,292; Non-Final Office Action dated Feb. 19, 2016; 8 pages.
U.S. Appl. No. 11/918,292; Non-Final Office Action dated Jun. 12, 2014; 12 pages.
U.S. Appl. No. 11/918,292; Notice of Allowance dated Aug. 18, 2016; 7 pages.
U.S. Appl. No. 11/918,296; Notice of Allowance dated Jun. 7, 2010; 7 pages.
U.S. Appl. No. 11/918,297; Examiner Initiated Interview Summary dated Jan. 25, 2012; 1 page.
U.S. Appl. No. 11/918,297; Non-Final Office Action dated Aug. 26, 2011; 26 oages.
U.S. Appl. No. 11/918,297; Notice of Allowance dated Jan. 25, 2012; 10 pages.
U.S. Appl. No. 12/769,570; Non-Final Office Action dated Jan. 26, 2011; 9 pages.
U.S. Appl. No. 12/769,570; Notice of Allowance dated Jul. 18, 2011; 7 pages.
U.S. Appl. No. 12/769,572; Advisory Action dated May 2, 2012; 3 pages.
U.S. Appl. No. 12/769,572; Advisory Action dated May 6, 2015; 18 pages.
U.S. Appl. No. 12/769,572; Final Office Action dated Jan. 6, 2015; 16 pages.
U.S. Appl. No. 12/769,572; Final Office Action dated Dec. 4, 2013; 7 pages.
U.S. Appl. No. 12/769,572; Final Office Action dated Feb. 29, 2012; 6 pages.
U.S. Appl. No. 12/769,572; Final Office Action dated May 4, 2011; 6 pages.
U.S. Appl. No. 12/769,572; Non-Final Office Action dated Dec. 10, 2010; 8 pages.
U.S. Appl. No. 12/769,572; Non-Final Office Action dated Aug. 19, 2014; 9 pages.
U.S. Appl. No. 12/769,572; Non-Final Office Action dated Aug. 28, 2014; 10 pages.
U.S. Appl. No. 12/769,572; Non-Final Office Action dated Oct. 20, 2011; 6 pages.
U.S. Appl. No. 12/769,572; Non-Final Office Action dated May 9, 2013; 6 pages.
U.S. Appl. No. 12/769,572; Notice of Allowance dated Apr. 29, 2014; 7 pages.
U.S. Appl. No. 12/769,572; Office Action dated Apr. 29, 2014.
U.S. Appl. No. 12/879,084; Notice of Allowance dated Feb. 11, 2011; 7 pages.
U.S. Appl. No. 12/879,084; Notice of Allowance dated Feb. 22, 2011; 4 pages.
U.S. Appl. No. 13/083,152; Non-Final Office Action dated Apr. 2, 2013; 10 pages.
U.S. Appl. No. 13/083,152; Notice of Allowance dated Aug. 22, 2013; 8 pages.
U.S. Appl. No. 13/085,793; Final Office Action dated Oct. 10, 2012; 8 pages.
U.S. Appl. No. 13/085,793; Non-Final Office Action dated Jan. 3, 2014; 13 pages.
U.S. Appl. No. 13/085,793; Non-Final Office Action dated Mar. 14, 2012; 9 pages.
U.S. Appl. No. 13/085,793; Non-Final Office Action dated Oct. 3, 2011; 6 pages.
U.S. Appl. No. 13/085,793; Notice of Allowance dated Aug. 21, 2014; 7 pages.
U.S. Appl. No. 13/107,498; Notice of Allowance dated Jun. 14, 2011; 8 pages.
U.S. Appl. No. 13/226,891; Notice of Allowance dated Jan. 9, 2012; 7 pages.
U.S. Appl. No. 13/306,336; Final Office Action dated Apr. 22, 2015; 11 pages.
U.S. Appl. No. 13/306,336; Final Office Action dated Feb. 26, 2014; 11 pages.
U.S. Appl. No. 13/306,336; Non-Final Office Action dated Jun. 23, 2014; 9 pages.
U.S. Appl. No. 13/306,336; Non-Final Office Action dated Nov. 14, 2014; 11 pages.
U.S. Appl. No. 13/306,336; Non-Final Office Action dated Jul. 23, 2013; 9 pages.
U.S. Appl. No. 13/379,704; Applicant Initiated Interview Summary dated Jun. 23, 2015; 4 pages.
U.S. Appl. No. 13/379,704; Declaration of Theresa Rosario-Jansen and David Erick Wright Under 37 C.F.R. Section 1.132 dated Jul. 24, 2014; 4 pages.
U.S. Appl. No. 13/379,704; Examiner Initiated Interview Summary dated Jul. 5, 2013; 1 page.
U.S. Appl. No. 13/379,704; Examiner Initiated Interview Summary dated May 6, 2016; 1 page.
U.S. Appl. No. 13/379,704; Final Office Action dated Oct. 10, 2014; 16 pages.
U.S. Appl. No. 13/379,704; Final Office Action dated Oct. 20, 2015; 20 pages.
U.S. Appl. No. 13/379,704; Non-Final Office Action dated Feb. 11, 2015; 21 pages.
U.S. Appl. No. 13/379,704; Non-Final Office Action dated Feb. 25, 2014; 11 pages.
U.S. Appl. No. 13/379,704; Non-Final Office Action dated Jul. 5, 2013; 9 pages.
U.S. Appl. No. 13/379,704; Notice of Allowance dated May 6, 2016; 10 pages.
U.S. Appl. No. 13/452,151; Examiner Initiated Interview Summary dated Jun. 19, 2012; 1 page.
U.S. Appl. No. 13/452,151; Notice of Allowance dated Jun. 19, 2012; 7 pages.
U.S. Appl. No. 13/461,170; Non-Final Office Action dated Feb. 4, 2013; 10 pages.
U.S. Appl. No. 13/461,170; Notice of Allowance dated May 17, 2013; 8 pages.
U.S. Appl. No. 13/623,512; Examiner Initiated Interview Summary dated Feb. 19, 2013; 1 page.
U.S. Appl. No. 13/623,512; Notice of Allowance dated Feb. 19, 2013; 7 pages.
U.S. Appl. No. 13/972,167; Non-Final Office Action dated Aug. 4, 2014; 10 pages.
U.S. Appl. No. 13/972,167; Notice of Allowance dated Dec. 26, 2014; 9 pages.
U.S. Appl. No. 14/462,368; Applicant Initiated Interview Summary dated Jun. 2, 2016; 3 pages.
U.S. Appl. No. 14/462,368; Final Office Action dated Apr. 20, 2017; 40 pages.
U.S. Appl. No. 14/462,368; Non-Final Office Action dated Sep. 2, 2016; 19 pages.
U.S. Appl. No. 14/671,246; Non-Final Office Action dated Apr. 6, 2016; 10 pages.

(56) References Cited

OTHER PUBLICATIONS

U.S. Appl. No. 14/671,246; Notice of Allowance dated Jan. 19, 2017; 8 pages.
U.S. Appl. No. 14/671,246; Notice of Allowance dated Nov. 8, 2016; 9 pages.
U.S. Appl. No. 14/806,494; Notice of Allowance dated Jun. 13, 2017; 8 pages.
U.S. Appl. No. 14/806,494; Notice of Allowance dated Sep. 27, 2017; 7 pages.
U.S. Appl. No. 15/356,046; Non-Final Office Action dated Aug. 9, 2018; 68 pages.
U.S. Appl. No. 15/356,046; Non-Final Office Action dated Dec. 27, 2018; 37 pages.
U.S. Appl. No. 15/649,398; Applicant Initiated Interview Summary dated Nov. 2, 2017; 3 pages.
U.S. Appl. No. 15/649,398; Non-Final Office Action dated Aug. 16, 2017; 11 pages.
U.S. Appl. No. 15/649,462; Non-Final Office Action dated Oct. 13, 2017; 10 pages.
U.S. Appl. No. 15/649,462; Notice of Allowance dated Jan. 29, 2018; 9 pages.
U.S. Appl. No. 15/649,478; Final Office Action dated Feb. 1, 2018; 8 pages.
U.S. Appl. No. 15/649,478; Non-Final Office Action dated Oct. 16, 2017; 10 pages.
U.S. Appl. No. 15/649,478; Notice of Allowance dated May 10, 2018.
U.S. Appl. No. 15/649,478; Notice of Allowance dated May 10, 2018; 8 pages.
U.S. Appl. No. 15/649,478; Notice of Allowance dated Sep. 11, 2018; 28 pages.
U.S. Appl. No. 15/649,488; Applicant Initiated Interview Summary dated Nov. 2, 2017; 3 pages.
U.S. Appl. No. 15/649,488; Examiner Initiated Interview Summary dated Jan. 19, 2018; 2 pages.
U.S. Appl. No. 15/649,488; Non-Final Office Action dated Sep. 11, 2017; 11 pages.
U.S. Appl. No. 15/649,488; Notice of Allowance dated Jan. 19, 2018; 10 pages.
U.S. Appl. No. 15/906,839; Examiner Initiated Interview Summary dated May 14, 2018; 02 pages.
U.S. Appl. No. 15/906,839; Notice of Allowance dated May 14, 2018; 09 pages.
U.S. Appl. No. 16/195,446; Non-Final Office Action, dated Oct. 2, 2019; 53 pages.
U.S. Appl. No. 16/195,446; Notice of Allowance, dated Jul. 1, 2020; 15 pages.
U.S. Appl. No. 16/202,743; Non-Final Office Action, dated Sep. 10, 2019; 45 pages.
U.S. Appl. No. 16/202,743; Notice of Allowance, dated Mar. 27, 2020; 13 pages.
U.S. Appl. No. 16/455,073 ; Non-Final Office Action, dated Apr. 29, 2020; 49 pages.
U.S. Appl. No. 16/777,625; Application as filed, dated Jan. 30, 2020; 78 pages.
U.S. Appl. No. 16/777,634; Application as filed, dated Jan. 30, 2020; 76 pages.
U.S. Appl. No. 16/777,646; Application as filed, dated Jan. 30, 2020; 295 pages.
U.S. Appl. No. 16/942,569; Application as filed, dated Jul. 29, 2020; 83 pages.
U.S. Appl. No. 60/670,573, filed Apr. 11, 2005.
U.S. Pat. No. 2,246,623, entitled "Puricase," filed Jul. 15, 1997, 1 page.
Varelas, J. et al., "Expression and Characterization of a Single Recombinant Proteoglycan Tandem Repeat Domain of Link Protein That Binds Zinc and Hyaluronate", Arch Biochem Biophys., 321(1):21-30, (1995).
Venkataseshan, V. et al., "Acute Hyperuricemic Nephropathy and Rental Failure after Transplantation", Nephron, 56:317-21, (1990).
Veronese, F. et al., "Branched and Linear Poly(Ethylene) Glycol: Influence of the Polymer Structure on Ezymological, Pharmacokinetic, and Immunological Properties of Protein Conjugates", J Bioact Compat Polym., 12:196-207, (1997).
Veronese, F. et al., "Introduction and Overview of Peptide and Protein Pegylation", Adv Drug Deliv Rev., 54(4):453-6, (2002).
Veronese, F. et al., "New Synthetic Polymers for Enzyme and Liposome Modification", ACS Publications, 680(Ch 13):182-92, (1997).
Veronese, F. et al., "Surface Modification of Proteins. Activation of Monomethoxy-Polyethylene Glycols by Phenylchloroformates and Modification of Ribonuclease and Superoxide Dismutase", Appl Biochem Biotechnol., 11(2):141-52, (1985).
Voet, D. et al., "Biochemistry", 2nd Ed., pp. 235-241, (1995).
Voshaar, M. et al., "Dutch Translation and Cross-Cultural Adaptation of the PROMIS® Physical Function Item Bank and Cognitive Pre-Test in Dutch Arthritis Patients", Arthritis Res Ther., 14(2):R47, (2012).
Wallrath, L. et al., "Molecular Characterization of the *Drosophila melanogaster* Urate Oxidase Gene, an Ecdysone-Repressible Gene Expressed Only in the Malpighian Tubules", Mol Cell Biol., 10(10):5114-27, (1990).
Waltrip, R. et al., "Pharmacokinetics And Pharmacodynamics Of Peg-Uricase In Patients With Hyperuricemia And Treatment Failure Gout", presented at the EULAR—Annual European Congress of Rheumatology, on Jun. 13-16, 2007 at Barcelona, Spain, Poster 358.
Waltrip, R. et al., "Weekly Flare Burden Index: A New Metric For Evaluating Gout Treatment", Ann Rheum Dis 2007; 66 (Suppl II):624, Abstract 748.
Wang, L. et al., "Purification and Characterization of Uricase, a Nitrogen-Regulated Enzyme, From Neurospora Crassa", Arch Biochem Biophys., 20(1):185-93, (1980).
Wang, X. et al., "Rat Urate Oxidase: Cloning and Structural Analysis of the Gene and 5'-Flanking Region", Gene, 97(2):223-9, (1991).
Ward et al., "Building activities of a repertoire of single immunoglobulin variable domains secreted from *Escherichia coli*," Nature, vol. 341, p. 544-546, Oct. 12, 1989.
Watanabe, T. et al., "A Simple Purification Method for Rat Liver Urate Oxidase", Anal Biochem., 89(2):343-7, (1978).
Wortmann, R. et al., "Gout and Hyperuricemia", Kelley's Textbook of Rheumatology, 6th ed., pp. 1339-1371, (2001).
Wu, E. et al., "Comorbidity Burden, Healthcare Resource Utilization, and Costs in Chronic Gout Patients Refractory to Conventional Urate-Lowering Therapy", Am J Ther., 19(6):e157-66, (2012).
Wu, X. et al., "Hyperuricemia and Urate Nephropathy in Urate Oxidase-Deficient Mice", Proc Natl Acad Sci U S A., 91(2):742-6, (1994).
Wu, X. et al., "Two Independent Mutational Events in the Loss of Urate Oxidase during Hominoid Evolution", J Mol Evol., 34(1):78-84, (1992).
Wu, X. et al., "Urate oxidase: primary structure and evolutionary implications", Proc Natl Acad Sci U S A., 86(23):9412-6, (1989).
Yamamoto, K. et al., "Nucleotide Sequence of the Uricase Gene from *Bacillus* sp. TB-90", J Biochem., 119(1):80-4, (1996).
Yamanaka, H. et al., "Optimal Range of Serum Urate Concentrations to Minimize Risk of Gouty Attacks during Anti-Hyperuricemic Treatment", Adv Exp Med Biol., 431:13-8, (1998).
Yasuda, Y. et al., "Biochemical and Biopharmaceutical Properties of Macromolecular Conjugates of Uricase with Dextran Polyethylene Glycol", Chem Pharm Bull., 38(7):2053-6, (1990).
Yeldandi, A. et al., "Human Urate Oxidase Gene: Cloning and Partial Sequence Analysis Reveal a Stop Codon within the Fifth Exon", Biochem Biophys Res Commun., 171(2):641-6, (1990).
Yelverton et al., "Bacterial synthesis of a novel human leukocyte interferon," Nucleic Acids Research, vol. 9, No. 3, p. 731,1981.
Yokoyama, S. et al., "Rapid Extraction of Uricase from Candida Utilis Cells by Use of Reducing Agent Plus Surfactant", Enzyme Microb Technol., 10(1):52-5, (1988).
Zhang, T. et al., "Affinity Extraction of BSA with Reversed Micellar System Composed of Unbound Cibacron Blue", Biotechnol Prog., 15(6):1078-82, (1999).

(56) References Cited

OTHER PUBLICATIONS

Zhang, W. et al., "Forward and Backward Extraction of BSA Using Mixed Reverse Micellar System of CTAB and Alkyl Halides", Biochem Eng J., 12(1):1-5, (2002).

Zhu J et al., Can Dynamic Contrast-Enhanced MRI (DCE-MRI) and Diffusion-Weighted MRI (DW-MRI) Evaluate Inflammation Disease, A Preliminary Study of Crohn's Disease, Medicine (Baltimore), Apr. 2016;95(14):e3239, pp. 1-9.

Abeles, A.M., "PEG-ing down (and preventing?) the cause of pegloticase failure," Arthritis Research & Therapy, Jun. 2014, 16:112., 2 pages.

Acetaminophen Extra Strength-acetaminophen tablet, Physicians Total Care, Inc., Apr. 29, 2016 (Apr. 29, 2016), pp. 1-4. Retrieved from the Internet:https://bit.ly/36wVn98 on Nov. 7, 2020 (Nov. 7, 2020).

Albert et al., "Increased Efficacy and Tolerability of Pegloticase in Patients With Uncontrolled Gout Co-Treated With Methotrexate: A Retrospective Study," Rheumatology and Therapy, Sep. 2020, vol. 7, pp. 639-648.

Alvarez-Lario et al., "Uric acid and evolution," Rheumatology, Jul. 2010, 49, pp. 2010-2015.

Applicant Initiated Interview Summary for U.S. Appl. No. 13/379,704, dated Jun. 23, 2015, 4 Pages.

Assadi F., "Managing New Onset Gout in Pediatric Renal Transplant Recipients: when, how, to what extent," Journal of Nephrology, Jul.-Aug. 2013, 26(4), pp. 624-628 2013.

Baraf et al., "Infusion-related reactions with pegloticase, a recombinant uricase for the treatment of chronic gout refractory to conventional therapy," Journal of Clinical Rheumatology, Dec. 2014, 20(8):427-432.

Baraf H.S.B., et al., "Resolution of Tophi With Intravenous Peguricase in Refractory Gout," Arthritis & Rheumatism, 2005, September Supplement, vol. 52, No. 9, p. S105.

Bessen et al., "Recapture and improved outcome of pegloticase response with methotrexate-A report of two cases and review of the literature," Seminars in Arthritis and Rheumatism, Aug. 2019, vol. 49, No. 1, pp. 56-61.

Botson et al., "Pegloticase in combination with methotrexate in patients with uncontrolled gout: A multicenter, open-label study (MIRROR)," The Journal of Rheumatology, May 2021;48:767-774, doi: 10.3899/jrheum.200460.

Botson et al., "Pretreatment and Coadministration with Methotrexate Improved Durability of Pegloticase (Krystexxa) Response: A Prospective, Proof-of-Concept, Case Series," Abstract, Arthritis Rheumatology, 2018; 70 (suppl 10), https://acrabstracts.org/abstract/pretreatment-andcoadministration- with-methotrexate-improved-durability-of-pegloticase-krystexxa-response-aprospective- proof-of-concept-case-series/, Accessed Sep. 11, 2018, 2 pages.

Botson et al., "Pretreatment and co-administration with methotrexate improved durability of pegloticase response: a prospective observational, proof-of-concept, case series [Abstract]," SAT0404 Annals of the Rheumatic Diseases, Jun. 2019, vol. 78, Issue Suppl. 2, A1289-A1290.

Botson et al., "Pretreatment and Co-Administration with Methotrexate Improved Durability of Pegloticase Response: A Prospective, Observational, Proof-of-Concept, Case Series," Poster presented at the 2018 Annual Scientific Meeting of the American College of Rheumatology, Oct. 19-24, 2018, 1 page.

Botson et al., "Pretreatment and co-administration with methotrexate improved durability of pegloticase response," Journal of Clinical Rheumatology, vol. 28, No. 1, Jan. 2022, e129-e134, doi: 10.1097/RHU.0000000000001639.

Bringham, M. D. et al., "Immunosuppressant Use and Gout in the Prevalent Solid Organ Transplantation Population," J of the American Society of Nephrology, Progress in Transplantation, Jun. 2020, 30(2), pp. 103-110.

Broadwell et al., "Community Practice Experiences with a Variety of Immunomodulatory Agents Co-Administered with Pegloticase for the Treatment of Uncontrolled Gout," Rheumatology and Therapy, Dec. 2022, 9(6), pp. 1549-1558.

Clive, D. M. "Renal Transplant-Associated Hyperuricemia and Gout," Journal of the American Society of Nephrology, May 1, 2000, vol. 11, pp. 974-979.

"EC 1.7.3.3, urate oxidase," BRENDA Enzyme Database, available via internet at www.brenda.uni-koeln.de/ (cited by USPTO Examiner in related U.S. Appl. No. 09/501,730, filed Feb. 10, 2000, in Notice of Allowance dated Jan. 13, 2004), 25 pages.

Estimated Glomerular Filtration Rate (eGFR), Kidney Health Australia, May 31, 2017, (Apr. 31, 2017), Retrieved from the Internet: https://kidney.org.au/uploads/resources/egfr-fact-sheet.pdf, Nov. 7, 2020 (Nov. 7, 2020). pp. 1-3.

European Search Report for European Application No. 05011069.1, dated Aug. 5, 2005, 6 Pages.

European Search Report for European Application No. 99938996.8, dated Mar. 4, 2002, 2 Pages.

Extended European Search Report for European Application No. 09175303.8, dated Jan. 26, 2010, 6 Pages.

Extended European Search Report for European Application No. 10158016.5, dated May 11, 2010, 10 Pages.

Extended European Search Report for European Application No. 10180428.4, dated Feb. 24, 2011, 7 Pages.

Extended European Search Report for European Application No. 10180672.7, dated Mar. 30, 2011, 6 Pages.

Extended European Search Report for European Application No. 10792756.8, dated Oct. 18, 2013, 04 Pages.

Extended European Search Report for European Application No. 17192971.4, dated Feb. 7, 2018, 8 Pages.

Extended European Search Report for European Application No. 17869608.4, dated Jul. 1, 2020, 10 Pages.

Extended European Search Report for European Application No. 18214393.3, dated Apr. 12, 2019, 5 Pages.

"FDA Approves KRYSTEXXA® (pegloticase) Injection Co-Administered with Methotrexate, Expaning the Labeling to Help More People with Uncontrolled Gout Achieve a Complete Response to Therapy," BENZINGA, Business Wire Press Releases, Jul. 8, 2022, 4 pages.

"FDA Approves KRYSTEXXA® (pegloticase) Injection Co-Administered with Methotrexate, Expaning the Labeling to Help More People with Uncontrolled Gout Achieve a Complete Response to Therapy," BioSpace, Jul. 8, 2022, 5 pages.

"FDA Approves KRYSTEXXA® (pegloticase) Injection Co-Administered with Methotrexate, Expaning the Labeling to Help More People with Uncontrolled Gout Achieve a Complete Response to Therapy," StreetInsider, Business Wire, Press Releases, Jul. 8, 2022, 3 pages.

"FDA Approves KRYSTEXXA® (pegloticase) Injection Co-Administered with Methotrexate, Expaning the Labeling to Help More People with Uncontrolled Gout Achieve a Complete Response to Therapy," Yahoo!Finance, Business Wire, Press Releases, Jul. 8, 2022, 4 pages.

"FDA Approves Pegloticase Injection Plus Methotrexate for Patients with Uncontrolled Gout," Rheumatology Network, Jul. 8, 2022, 1 page.

"FDA approves peglioticase, methotrexate combo in patients with uncontrolled gout," Healio Rheumatology, Jul. 8, 2022, 2 pages.

"FDA Approves Peglioticase Plus Methotrexate for Uncontrolled Gout," HCPLive, Jul. 8, 2022, 1 page.

"FDA approves pegloticase injection coadministered with methotrexate for gout," AJMC, Jul. 8, 2022, 2 pages.

"FDA decisions to watch in rheumatology in Second Half of 2022," Rheumatology Network, Jun. 29, 2022, 3 pages.

File History of U.S. Pat. No. 7,056,713.

Hershfield M. et al., "Induced and Pre-Existing Anti-Polyethylene Glycol Antibody in a Trial of Every 3-Week Dosing of Pegloticase for Refractory Gout, including in organ transplant recipients," Arthritis Research & Therapy, Mar. 2014, 16(2), pp. 1-11.

Highlights of Prescribing Information for Allegra (fexofenadine hydrochloride) tablets, ODT 1-18, orally disintegrating tablets) and oral suspension, Jul. 31, 2007 (Apr. 31, 2007), pp. 1-19. Retrieved from the Internet www.accessdata.fda.gov/drugsatfda_docs/label/2008/020872s018,021963s0021bl.pdf on Nov. 7, 2020 (Nov. 7, 2020).

(56) References Cited

OTHER PUBLICATIONS

"Horizon gets FDA approval for Krystexxa's use with methotrexate for uncontrolled gout," Seeking Alpha, Ravikash, SA News Editor, Jul. 8, 2022, 2 pages.
Horizon, "Horizon Therapeutics plc announces FDA has granted priority review of the supplemental biologies license application (sBLA) for the concomitant use of KRYSTEXXA® (pegloticase injection) plus methotrexate for people living with uncontrolled gout," Mar. 7, 2022, 3 pages.
"Horizon's Krystexxa wins FDA combo nod to fight drug resistance," Fierce Pharm, Jul. 8, 2022, 3 pages.
"Horizon nabs FDA expanded label for gout med Krystexxa," Endpoints, Jul. 8, 2022, 2 pages.
"Horizon Therapeutics: FDA Approves Expanded Labeling for KRYSTEXXA With Methotrexate," Nasdaq, Jul. 8, 2022, 1 page.
"Horizon Therapeutics: FDA approves expanded labeling for KRYSTEXXA with methotrexate," RTTNews, Published Jul. 8, 2022, 5 pages.
"Horizon therapeutics receives FDA approval for uncontrolled gout candidate," BENZINGA, Jul. 8, 2022, 7 pages.
International Preliminary Report on Patentability for International Application No. PCT/US2020/015956, dated Aug. 12, 2021, 10 Pages.
International Preliminary Report on Patentability for International Application No. PCT/US2020/015958, dated Aug. 12, 2021, 12 Pages.
International Preliminary Report on Patentability for International Application No. PCT/US2020/015959, dated Aug. 12, 2021, 13 Pages.
International Preliminary Report on Patentability for International Application No. PCT/US2020/048803, dated Mar. 10, 2022, 9 Pages.
International Search Report and Written Opinion for International Application No. PCT/US2020/015956, dated May 5, 2020, 13 Pages.
International Search Report and Written Opinion for International Application No. PCT/US2020/048803, dated Nov. 24, 2020, 13 Pages.
International Search Report and Written Opinion for International Application No. PCT/US2021/045350, dated Dec. 27, 2021, 10 Pages.
International Search Report for International Application No. PCT/US2000/017398, dated Dec. 6, 2000, 3 Pages.
Keenan et al., "The effect of immunomodulators on the efficacy and tolerability of pegloticase: a systematic review," Seminars in Arthritis and Rheumatism, vol. 51, No. 2, Apr. 2021, pp. 347-352.
Khanna et al., "2012 American College of Rheumatology Guidelines for Management of Gout Part I: Systematic Non-Pharmacologic and Pharmacologic Therapeutic Approaches to Hyperuricemia," Arthritis Care & Research, Oct. 2012, 64(10), pp. 1431-1466 (28 pages).
Khanna et al., "2012 American College of Rheumatology Guidelines for Management of Gout Part II: Therapy and Anti-Inflammatory Prophylaxis of Acute Gouty Arthritis," Arthritis Care & Research, Oct. 2012, 64(10), pp. 1447-1461 (23 pages).
Khanna et al., "Reducing Immunogenicity of Pegloticase (RECIPE) with Concomitant use of Mycophenolate Mofetil in Patients with Refractory Gout-a Phase II Double Blind Ramdomized Controlled Trial," ACR Convergence 2020, Abstract #0952, Nov. 2020, 5 pages.
Khanna et al., "Reducing Immunogenicity of Pegloticase (RECIPE) with Concomitant use of Mycophenolate Mofetil in Patients with Refractory Gout-a Phase II Double Blind Ramdomized Controlled Trial," ACR Convergence Where Rheumatology Meets, Abstract #0952, Nov. 2020, Final Presentation, 17 pages.
Khanna et al., "Reducing Immunogenicity of Pegloticase with Concomitant use of Mycophenolate Mofetil in Patients with Refractory Gout: A Phase II, Ramdomized, Double-Blind, Placebo-Controlled Trial," Arthritis & Rheumatology, vol. 73, No. 8, Aug. 2021, pp. 1523-1532.
KRYSTEXXA (pegloticase) [prescribing information] Horizon, Apr. 2012, 14 pages.
"Krystexxa plus methotrexate approved for uncontrolled gout," MedMDS, Jul. 8, 2022, 4 pages.
"Krystexxa plus methotrexate approved for uncontrolled gout," MPR, Jul. 8, 2022, 4 pages.
Majijhoo et al., "Comparison of two corticosteriod pre-infusion regimes for pegloticase in the United States: A retrospective analysis in community rheumatology practices," Drugs Real World Outcomes, Dec. 2019;6(4):165-171.
Majjhoo A., et al., "Prophylaxis for Infusion Reactions to Pegloticase: An Analysis of Two Different Corticosteroid Pre-Infusion Regimens in US Community Rheumatology Practices," ACR/ARHP Annual Meeting, Abstract No. 213, Prophylaxis to Pegloticase, Sep. 28, 2016, 4 Pages, Retrieved from URL: https://acrabstracts.org/abstract/.
Milgroom, A. et al., "Immunosuppressant Use and Gout in the Prevalent Solid Organ Transplant Population," Journal of the American Society of Nephrology, Oct. 2018, 29:152 Abstract TH-P0160, 3 pages.
Mountain View Pharmaceuticals, Inc., "Puricase.rtm.," U.S. Trademark Registration No. 2,246,623 (report obtained from U.S. Trademark Electronic Search System (TESS), Dec. 5, 2001), 1 page.
"$NZNP—Horizon gets FDA approval for Krystexxa's use with methotrexate for uncontrolled gout," Breaking News ©Marketcurrents, Jul. 8, 2022, SANewsTwitter, 1 page.
Saag et al. "Initial results of a clinical study to determine whether a tolerizing regimen of pegloticase can increase the frequency of subjects having sustained lowering of serum urate," American College of Rheumatology, Abstract 1141, Sep. 2017, 2 pages.
Schlesinger et al., "Evaluation of proposed criteria for remission and evidence-based development of criteria for complete response in patients with chronic refractory gout," ACR Open Rheumatology, Jun. 2019, vol. 1, No. 4, pp. 236-243, doi: 10.1002/acr2.1025.
Sundy S., et al., Arthritis & Rheumatism, Sep. 2005, vol. 52, No. 9 (Supplement), Abstract Supplement, Annual Scientific Meeting, San Diego, California, Nov. 12-17, 2005, Abstract #1836, 3 Pages.
"The @US_FDA's decision on the co-treatment of pegloticase (#Krystexxa) plus methotrexate (#MTX) for patients with uncontrolled #gout was based on the phase 4 MIRROR clinical trial," HCPLive Tweet Twitter, Jul. 8, 2022, 1 page.
"The @US_FDA expanded the #pegloticase label to include the co-treatment of pegloticase (KRYSTEXXA) injection plus methotrexate in patients with uncontrolled #gout. @HorizonNews," Rheumatology Network Tweet Tweeter, Jul. 8, 2022, 1 page.
Tutton, R. et al., "Pharmacogenomic Biomarkers in Drug Labels: What do they tell us?," Pharmacogenomics, Feb. 2014, 15(3), pp. 297-304.
Verma et al., "Folate Conjugated Double Liposomes Bearing Prednisolone and Methotrexate for Targeting Rheumatoid Arthritis," Pharmaceutical Research, Aug. 2019, 36(8):123, pp. 1-13.
Vermeire et al., "Effectiveness of concomitant immunosuppresive therapy in suppressing the formation of antibodies to infliximab in Crohn's disease," Gut, Jan. 2007, vol. 56, pp. 1226-1231.
WHO Drug Information, vol. 21, No. 4, 2007, List 98, p. 344.
Wuthrich, H et al., "Guidelines for the Treatment of Gout: A Swiss Perspective," Swiss Medical Weekly 146, (Year: 2016), pp. 1-7.

METHODS AND KITS FOR PREDICTING INFUSION REACTION RISK AND ANTIBODY-MEDIATED LOSS OF RESPONSE BY MONITORING SERUM URIC ACID DURING PEGYLATED URICASE THERAPY

CROSS REFERENCE TO RELATED APPLICATIONS

This application is a continuation of U.S. application Ser. No. 16/195,446, filed Nov. 19, 2018, now U.S. Pat. No. 10,823,727, which is a continuation of U.S. application Ser. No. 15/906,839, filed on Feb. 27, 2018, now U.S. Pat. No. 10,139,399, which is a continuation of U.S. application Ser. No. 15/165,318, filed on May 26, 2016, now abandoned, which is a continuation of U.S. application Ser. No. 13/379,704, filed on Aug. 8, 2012, now U.S. Pat. No. 9,377,454, which is a national stage filing of International Application No. PCT/US2010/004008, filed on Jun. 25, 2010, which claims priority to and benefit of U.S. Provisional Application No. 61/269,669, filed on Jun. 25, 2009, U.S. Provisional Application No. 61/248,698, filed on Oct. 5, 2009, U.S. Provisional Application No. 61/298,718, filed on Jan. 27, 2010, the contents of which are incorporated herein by reference in their entireties.

FIELD OF THE INVENTION

This invention relates to methods for monitoring immunogenicity and infusion reactions during PEGylated uricase therapy.

BACKGROUND OF THE INVENTION

Throughout this application, various publications are referenced within the text. The disclosure of these publications in their entireties are hereby incorporated by reference into this application in order to more fully describe the state of the art as known to those skilled in therein as of the date of the invention described and claimed herein.

Gout is a chronic disorder of urate metabolism resulting in deposition of monosodium urate crystals in the joints and soft tissues, with accompanying inflammation and eventually, in some patients, destructive, chronic arthropathy. Gout is the most prevalent form of arthritis in men and is increasing in incidence and prevalence among older persons of both genders. Chronic gout refractory to Conventional Therapy (GRT) is an uncommon but severe outcome of progressive gout resulting from demonstrated intolerance of or refractoriness to available therapy to prevent urate crystal deposition by reducing and maintaining serum urate levels in a subsaturating range.

Elevated serum urate is a hallmark biochemical marker of gout. Persistently elevated plasma uric acid (PUA) or serum uric acid (SUA) levels result in deposition of uric acid in joints and soft tissues. As the total body burden of uric acid increases, signs and symptoms of gout result, including arthritis, characterized by recurrent painful gout flares, development of tophi and joint deformities with resultant chronic pain/inflammation and consequent loss of physical function.

The efficacy end point of successful PEGylated uricase therapy is normalization of serum uric acid levels in CGR patients while maintaining low immunogenicity profile and low risk of infusion reactions associated with intravenous injections of PEGylated uricase. However, given that the loss of PEGylated uricase effect and infusion reactions can accompany PEGylated uricase administration, clinicians should be advised as to the proper time point at which to discontinue therapy. Thus, there is a need in the art for new methods to guide clinicians when to discontinue the PEGylated uricase therapy in order to minimize infusion reactions and their associated safety risks.

SUMMARY OF THE INVENTION

The present invention provides for methods of preventing infusion reactions during PEGylated uricase therapy in a patient comprising the steps of a) administering to said patient PEGylated uricase; b) obtaining a biological sample from said patient; c) determining uric acid levels in said biological sample; and d) indicating that therapy may be discontinued to prevent infusion reactions when said uric acid level is more than about 4 mg/dl. In one aspect of the invention, PEGylated uricase therapy may be discontinued when said uric acid level is more than about 5 mg/dl. In another aspect of the invention, PEGylated uricase therapy may be discontinued when said uric acid level is more than about 6 mg/dl and in yet another aspect of the invention, the PEGylated uricase therapy may be discontinued when said uric acid level is more than about 7 mg/dl.

In another aspect of the invention, the PEGylated uricase is administered at a dosage of about 8 mg every 2 weeks. In one embodiment, the PEGylated uricase is administered at a dosage of about 8 mg every 3 weeks. In another embodiment, the PEGylated uricase is administered at a dosage of about 8 mg every 4 weeks. In yet another embodiment, the PEGylated uricase is administered at a dosage of about 4 mg every 2 weeks. In yet another embodiment, the PEGylated uricase is administered at a dosage of about 12 mg every 4 weeks.

The methods of the present invention provides for biological sample selected from the group consisting of blood, serum and plasma. In one embodiment, said uric acid levels in said biological sample are determined at least 2 hours after administration as defined in step (a). In another embodiment, said uric acid levels in said biological sample are determined at least 6 hours after administration as defined in step (a). In yet another embodiment, said uric acid levels in said biological sample are determined at least 24 hours after administration as defined in step (a). In yet another embodiment, said uric acid levels in said biological sample are determined 2 weeks after administration as defined in step (a). And in yet another embodiment, said uric acid levels in said biological sample are determined 4 weeks after administration as defined in step (a).

The methods of the present invention relate to patients suffering from gout. In one embodiment, said gout is refractory. In another embodiment, said gout is chronic or tophaceous. In yet another embodiment, the PEGylated uricase is administered intravenously.

The methods of the present invention predict whether a patient treated with PEGylated uricase will develop infusion reaction, wherein the method comprises the steps of: a) administering to said patient PEGylated uricase; b) obtaining a biological sample from said patient; c) determining uric acid levels in said biological sample; and d) indicating that uric acid level is associated with a lower likelihood of infusion reaction when said level is maintained at less than about 4 mg/dl or indicating that said determined uric acid level is associated with a higher likelihood of infusion reaction at a time point when said level is measured at least about 4 mg/dl.

In one aspect of the invention, said uric acid level is associated with a lower likelihood of infusion reaction when said level is maintained at less than about 5 mg/dl or said determined uric acid level is associated with a higher likelihood of infusion reaction at a time point when said level is measured at least about 5 mg/dl. In another aspect of the invention, said uric acid level is associated with a lower likelihood of infusion reaction when said level is maintained at less than about 6 mg/dl or said determined uric acid level is associated with a higher likelihood of infusion reaction when said level is measured at least about 6 mg/dl. In yet another aspect of the invention, said uric acid level is associated with a lower likelihood of infusion reaction when said level is maintained at less than about 7 mg/dl or said uric acid level is associated with a higher likelihood of infusion reaction at a time point when said uric acid level is measured at least about 7 mg/dl.

In another aspect of the invention, the uric acid levels in said biological sample are determined at least 3 days after the administration as defined in step (a). In another aspect of the invention, the uric acid levels in said biological sample are determined at least 1 week after the administration as defined in step (a). In another aspect of the invention, the uric acid levels in said biological sample are determined at least 2 weeks after the administration as defined in step (a). In another aspect of the invention, the uric acid levels in said biological sample are determined at least 4 weeks after the administration as defined in step (a).

The methods of the present invention predict whether a patient treated with PEGylated uricase will develop antibody-mediated PEGylated uricase clearance without measuring anti-PEGylated uricase and anti-PEG antibodies titer, wherein the method comprises the steps of a) administering to said patient PEGylated uricase; b) obtaining a biological sample from said patient; c) determining uric acid levels in said biological sample; and d) indicating that uric acid level is associated with a lower likelihood of antibody-mediated PEGylated uricase clearance when said level is maintained at less than about 4 mg/dl or indicating that said determined uric acid level is associated with a higher likelihood of antibody-mediated PEGylated uricase clearance at a time point when said uric acid level is measured at least about 4 mg/dl.

In one aspect of the invention, said uric acid level is associated with a lower likelihood of antibody-mediated PEGylated uricase clearance when said level is maintained at less than about 5 mg/dl or indicating that said determined uric acid level is associated with a higher likelihood of antibody-mediated PEGylated uricase clearance at a time point when said uric acid level is measured at least about 5 mg/dl. In another aspect of the invention, said uric acid level is associated with a lower likelihood of antibody-mediated PEGylated uricase clearance when said level is maintained at less than about 6 mg/dl or indicating that said determined uric acid level is associated with a higher likelihood of antibody-mediated PEGylated uricase clearance at a time point when said uric acid level is measured at least about 6 mg/dl. In yet another aspect of the invention, said uric acid level is associated with a lower likelihood of antibody-mediated PEGylated uricase clearance when said level is maintained at less than about 7 mg/dl or indicating that said determined uric acid level is associated with a higher likelihood of antibody-mediated PEGylated uricase clearance at a time point when said uric acid level is measured at least about 7 mg/dl.

In another aspect of the invention, the uric acid levels in said biological sample are determined at least 3 days after the administration as defined in step (a). In another aspect of the invention, the uric acid levels in said biological sample are determined at least 1 week after the administration as defined in step (a). In another aspect of the invention, the uric acid levels in said biological sample are determined at least 2 weeks after the administration as defined in step (a). In another aspect of the invention, the uric acid levels in said biological sample are determined at least 4 weeks after the administration as defined in step (a).

DETAILED DESCRIPTION OF THE INVENTION

Definitions

Figure 1:
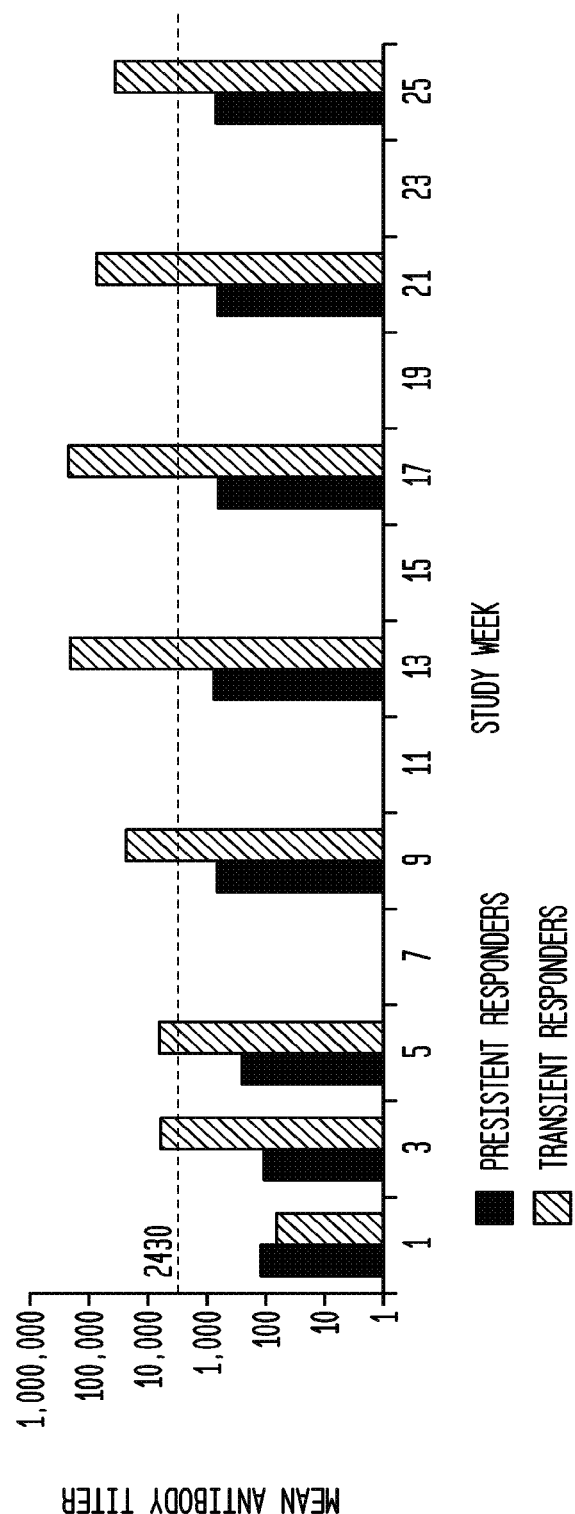
FIG. 1 shows mean anti-pegloticase antibody titer in patients receiving pegloticase every 2 Weeks.

In accordance with this detailed description, the following abbreviations and definitions apply. It must be noted that as used herein, the singular forms "a," "an," and "the" include plural referents unless the context clearly dictates otherwise.

It had been surprisingly discovered that monitoring SUA levels predicts antibody-mediated loss of response and the majority of infusion reactions during PEGylated uricase therapy. It has been found that most infusion reactions occurred after loss of SUA response. Therefore, routine monitoring of SUA can be used to prospectively identify patients receiving PEGylated uricase who no longer benefit from treatment and are at a greater risk for infusion reactions.

The term "therapeutic efficacy" as used herein refers to the effectiveness of a particular treatment regimen. Specifically, therapeutic efficacy is defined by achieving serum urate levels less or about 6 mg/dl. This includes a balance of efficacy, toxicity (e.g., side effects and patient tolerance of a formulation or dosage unit), patient compliance, and the like.

The terms "treating," "treatment," and the like are used herein to refer to obtaining a desired pharmacological and physiological effect. The effect can be prophylactic in terms of preventing or partially preventing a disease, symptom, or condition thereof and/or can be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a patient which can be predisposed to the disease but has not yet been diagnosed as having it, i.e., causing the clinical symptoms of the disease not to develop in a patient that can be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein the term "immunogenicity" refers to the induction of an immune response by an injected preparation of PEG-modified or unmodified uricase (the antigen), while "antigenicity" refers to the reaction of an antigen with preexisting antibodies. Collectively, antigenicity and immunogenicity are referred to as "immunoreactivity." In previous studies of PEGylated uricase, immunoreactivity is assessed by a variety of methods, including: 1) the reaction in vitro of PEGylated uricase with preformed antibodies; 2) measurements of induced antibody synthesis; and 3) accelerated clearance rates of PEGylated uricase after repeated injections.

As used herein the term "infusion reaction" is an undesired and unintended effect of a PEGylated uricase occurring within 2 hours after the PEGylated uricase or placebo infusion that cannot be reasonably attributed to another cause. In particular, an adverse drug reaction occurs at doses used for prophylaxis, diagnosis or therapy.

The PEGylated uricase conjugates of the present invention are useful for lowering the levels of uric acid in the body fluids and tissues of mammals, preferably humans, and can thus be used for treatment of elevated uric acid levels associated with conditions including gout, tophi, renal insufficiency, organ transplantation and malignant disease. PEGylated uricase conjugates can be injected into a mammal having excessive uric acid levels by any of a number of routes, including intravenous, subcutaneous, intradermal, intramuscular and intraperitoneal routes.

In once embodiment, PEGylated uricase is administered in a pharmaceutically acceptable excipient or diluent at 8 mg every two weeks. In another embodiment, PEGylated uricase can be administered at 8 mg every four weeks. In yet another embodiment, PEGylated uricase can be administered at 8 mg every three weeks.

In the other aspect of the invention, PEGylated uricase can be administered at 4 mg every two weeks. In yet another aspect of the invention, PEGylated uricase can be administered at 12 mg every four weeks.

Pharmaceutical formulations containing PEGylated uricase can be prepared by conventional techniques, e.g., as described in Gennaro, A R (Ed.) (1990) Remington's Pharmaceutical Sciences, 18th Edition Easton, Pa.: Mack Publishing Co. Suitable excipients for the preparation of injectable solutions include, for example, phosphate buffered saline, lactated Ringer's solution, water, polyols and glycerol. Pharmaceutical compositions for parenteral injection comprise pharmaceutically acceptable sterile aqueous or non-aqueous liquids, dispersions, suspensions, or emulsions as well as sterile powders for reconstitution into sterile injectable solutions or dispersions just prior to use. These formulations can contain additional components, such as, for example, preservatives, solubilizers, stabilizers, wetting agents, emulsifiers, buffers, antioxidants and diluents.

PEGylated uricase can also be provided as controlled-release compositions for implantation into an individual to continually control elevated uric acid levels in body fluids. For example, polylactic acid, polyglycolic acid, regenerated collagen, poly-L-lysine, sodium alginate, gellan gum, chitosan, agarose, multilamellar liposomes and many other conventional depot formulations comprise bioerodible or biodegradable materials that can be formulated with biologically active compositions. These materials, when implanted or injected, gradually break down and release the active material to the surrounding tissue. For example, one method of encapsulating PEGylated uricase comprises the method disclosed in U.S. Pat. No. 5,653,974, which is hereby incorporated by reference. The use of bioerodible, biodegradable and other depot formulations is expressly contemplated in the present invention. The use of infusion pumps and matrix entrapment systems for delivery of PEGylated uricase is also within the scope of the present invention. PEGylated uricase can also advantageously be enclosed in micelles or liposomes. Liposome encapsulation technology is well known in the art. See, e.g., Lasic, D, et al., (Eds.) (1995) Stealth Liposomes. Boca Raton, Fla.: CRC Press.

The uricase used in PEGylated uricase can comprise a mammalian uricase amino acid sequence truncated at the amino terminus or the carboxy terminus or both the amino and carboxy termini by about 1-13 amino acids and can further comprise an amino acid substitution at about position 46. The truncated uricase can further comprise an amino terminal amino acid, wherein the amino terminal amino acid is alanine, glycine, proline, serine, or threonine as described in PCT/US2006/013660 and U.S. provisional application Ser. No. 60/670,573, which are hereby incorporated herein by reference in their entireties.

Phase 3 study was completed as indicated in the Examples. In one aspect of the invention, normalization of uric acid of at least about 3.5 mg/dL was selected as the primary outcome measure to reflect the pharmacodynamic effect of PEGylated uricase. In another aspect of the invention, normalization of uric acid of at least about 4.0 mg/dL was selected as the primary outcome measure to reflect the pharmacodynamic effect of PEGylated uricase. In yet another aspect of the invention, normalization of uric acid of at least about 5.0 mg/dL was selected as the primary outcome measure to reflect the pharmacodynamic effect of PEGylated uricase. In yet another aspect of the invention, normalization of uric acid of at least about 6.0 mg/dL was selected as the primary outcome measure to reflect the pharmacodynamic effect of PEGylated uricase. In another aspect of the invention, normalization of uric acid of at least about 7.0 mg/dL was selected as the primary outcome measure to reflect the pharmacodynamic effect of PEGylated uricase.

It is know that persistently elevated plasma uric acid (PUA) or serum uric acid (SUA) levels result in deposition of uric acid in joints and soft tissues. As the total body burden of uric acid increases, signs and symptoms of gout result, including arthritis, characterized by recurrent painful gout flares, development of tophi and joint deformities with resultant chronic pain/inflammation and consequent loss of physical function.

PEGylated uricase 8 mg q2 wk results in marked decreases in uric acid (PUA and SUA) which is associated with complete resolution of tophi in some patients and decreased tender joint counts. Treatment is also associated with a decrease in the incidence and frequency of gout flares after 3 months of therapy compared with placebo, with continued reductions in flare incidence and frequency with long term administration, up to at least 18 months. These benefits occur in patients with chronic and often severe disease who have no other currently available therapy. Persistent responders are those patients who maintain lowered SUA values in response to repeated PEGylated uricase infusions. Maintenance of lowered SUA values is associated with no or low anti-PEGylated uricase antibody response (titers<2430).

The relationship between measured plasma uric acid (PUA) and serum uric acid (SUA) values was evaluated from serial samples from all patients in phase 3 studies. The rationale for this evaluation related to the use of PUA as the measure for the primary endpoint for all PEGylated uricase trials while SUA is used in clinical practice. The handling and processing of samples for PUA determination is much more involved, and this processing was performed at low temperature and utilized trichloroacetic acid to inactivate and precipitate PEGylated uricase so the drug did not continue to oxidize uric acid. Nevertheless, the experimental results unequivocally show a close correlation between both uric acid values at all time points and irrespective of the uric acid values.

An infusion reaction was defined as any adverse event that occurred during or within 2 hours after the PEGylated uricase or placebo infusion that could not be reasonably attributed to another cause. Although there was protocol-specified infusion reaction prophylatic treatment, infusion reactions occurred in 26% of patient treated with PEGylated uricase q2 wk and 40% with PEGylated uricase q4 wk.

Anti-PEGylated uricase antibodies were observed in about 90% of patients treated with PEGylated uricase. Antibodies at higher titers (>1:2430) were associated with increased clearance of PEGylated uricase and loss of PEGylated uricase activity, but high titers were frequently not detected until some time after uric acid levels were increased, sometimes lagging by several weeks after the loss of PEGylated uricase response. Patients who initially responded to PEGylated uricase and lost response at later time points were referred to as transient responders, in contrast to patients who maintained urate lowering activity of PEGylated uricase throughout the study and were termed persistent responders. The rise in PUA precedes the evidence of higher titers of antibodies.

Patients who developed high antibody titers (but not lower titers) had a high likelihood of loss of PUA response. The evidence of a transient response was clear in all patients by month 4 following initiation of therapy. The clinical effects of immunogenicity are easily detected by regular monitoring of SUA levels during the first few months of therapy. Although those patients who developed higher titer antibodies had a higher incidence of infusion reactions, there was no clear relationship between antibody titer and severity of infusion reactions.

The results herein indicate the development of high titer anti-PEGylated uricase antibodies and any titer of anti-PEG explains the loss of the SUA/PUA response. In patients that eventually develop higher titers of antibodies to PEGylated uricase there a higher risk of infusion reactions. Importantly, most infusion reactions occur after the loss of SUA/PUA response and, as a result, careful monitoring of SUA can avoid unnecessary dosing and also prevent the majority of infusion reactions. The loss of effect in most transient responders occurs within the first 4 months, so monitoring serum uric acid during that time period is critical. Finally, the loss of effect of PEGylated uricase can frequently occur before the rise in anti-PEGylated uricase antibody titer, so that there is no correlation between the titer of anti-PEGylated uricase antibody, or the presence of any titer anti-PEG antibody, before or at the time of loss of a SUA/PUA response. The lack of association between antibody titer and the SUA/PUA response confirms the ineffectiveness of monitoring antibody titers during PEGylated uricase therapy of patients with treatment failure gout.

Example 1—Immunogenicity and Infusion Reaction Profiles of Pegloticase Intravenous Administration at 8 mg Every 2 Weeks Material, Methods and Design of Clinical Study.
Investigational Drug Pegloticase, a PEGylated uricase used in this example, consists of a recombinant mammalian uricase (primarily porcine, with C-terminal sequence from baboon uricase), conjugated with multiple strands of monomethoxy PEG of average molecular weight 10 kDa (10 K mPEG) per subunit of tetrameric enzyme (Kelly S J, et al. J Am Soc Nephrol 2001, 12:1001-1009; and Ganson N J, et al. Arthritis Res Ther 2005, 8(1):R12).
Phase III Study Design.
Patients:

Multi-center (45 sites), replicate, double-blind, placebo-controlled, studies were performed in patients with symptomatic gout.

All patients received an intravenous (i.v.) infusion (pegloticase or placebo) every 2 weeks. Treatment groups consisted of placebo (N=43), pegloticase 8 mg i.v. every 2 weeks (q2 wks) (N=84).

All patients reported a medical history in which allopurinol therapy was contraindicated (e.g., history of hypersensitivity, intolerance, or toxicity) or had not been effective, defined as failure to normalize SUA with ≥3 months allopurinol treatment at the maximum labeled dose (800 mg/day) or at a medically appropriate lower dose based on toxicity or dose-limiting co-morbidity. The major exclusion criteria at entry included: unstable angina, uncontrolled arrhythmia, non-compensated congestive heart failure, uncontrolled hypertension (above 150/95 mmHg), dialysis, organ transplant recipient, pregnancy and other.

For these experiments, all patients discontinued all urate-lowering therapies≥one week prior to randomization, and refrained from using such agents throughout the study.

All patients received prophylaxis for infusion reactions (IR): oral fexofenadine (60 mg evening prior and immediately before infusion), and acetaminophen (1000 mg) and hydrocortisone IV (200 mg) prior to each infusion. Study medication was administered in 250 mL saline over 2 to 4 hours total infusion time.
Immunogenicity The qualitative and quantitative ELISA assays used for study sample analysis were validated to Good Laboratory Practices following accepted immunology assay guidance (Mire-Sluis et al). Samples for antibody determination using ELISA assays were collected from all patients at baseline and at Weeks 3, 5, 9, 13, 17, 21 and 25 after initiation of treatment with pegloticase or placebo.
Detection of Anti-Pegloticase Antibody.

For determination of total pegloticase antibodies, study samples were diluted 1/30 in assay buffer and assayed using microtiter ELISA plate wells coated with either pegloticase or PEG. A human serum containing pegloticase antibodies was used as a positive control for detection of total pegloticase antibody as well as IgM and IgG antibodies. The combination of rabbit anti-human IgM and IgG was used as secondary antibodies, whereas each individually was employed for assay of IgM and IgG anti-pegloticase antibodies, respectively (Sigma, St. Louis, Mo.)

For these experiments, horseradish peroxidase-conjugated mouse monoclonal antibody to rabbit IgG was used for detection. Microtiter plate wells coated with purified human IgG and IgM served as immunoglobulin positive controls for the binding of anti-human IgG and anti-human IgM secondary antibodies.

Drug interference was determined to be 300 µg/mL which is much higher than the measured circulating pegloticase concentration determined in the study samples. Therefore, circulating pegloticase would not be anticipated to interfere with the measurement of anti pegloticase antibodies.
Properties of the Anti-Pegloticase Antibodies.

For the majority of samples from the phase 3 patients, the antibody response involved both IgM and IgG antibodies.
Detection of Anti-Pegloticase Antibodies.

For these experiments, the anti-pegloticase analysis methodology parallels the general method for the anti-pegloticase antibody assay, with the exception that a surrogate positive control was used for the initial study sample analyses. This positive control consisted of a mixture of mouse monoclonal anti-PEG IgG1 and anti-PEG IgM antibodies, added to pooled human serum and diluted 1/10 in blocker casein in PBS. A human positive control was introduced in the assay towards the end of the study sample analysis. For these experiments, the assay sensitivity was 500 ng/mL and is also reflected in a low false detection rate of 8.6%.
Safety Evaluations—Infusion Reactions.

For these experiments, infusion reactions were defined as any adverse event that occurred during or within 2 hours after the infusion of blinded study medication that could not be reasonably attributed to other causes. Infusion reactions occurred during the infusion of pegloticase and placebo. Signs and symptoms of serious infusion reactions included: dyspnea, hypotension, hypertension, swelling, brochospasm, chest pain, nausea, vomiting and abdominal pain and cramping.

As shown in FIG. 1, at all time points after dosing, the persistent responders in the q2 wk group had lower mean anti-pegloticase antibody titers compared to the transient responders. For example, it was observed that patients with anti-pegloticase antibody titer<1:810 at any time during the study were associated with persistent response. Thus, 68% of the q2 week persistent responders had titers that never exceeded a titer of 1:810. On the other hand, only 23% of the q2 week transient responders had titers<1:810. Therefore, low titer was associated with persistent response.
Anti-Pegloticase Antibody Effects on Pegloticase Pharmacokinetics and Pharmacodynamics.

Figure 2:
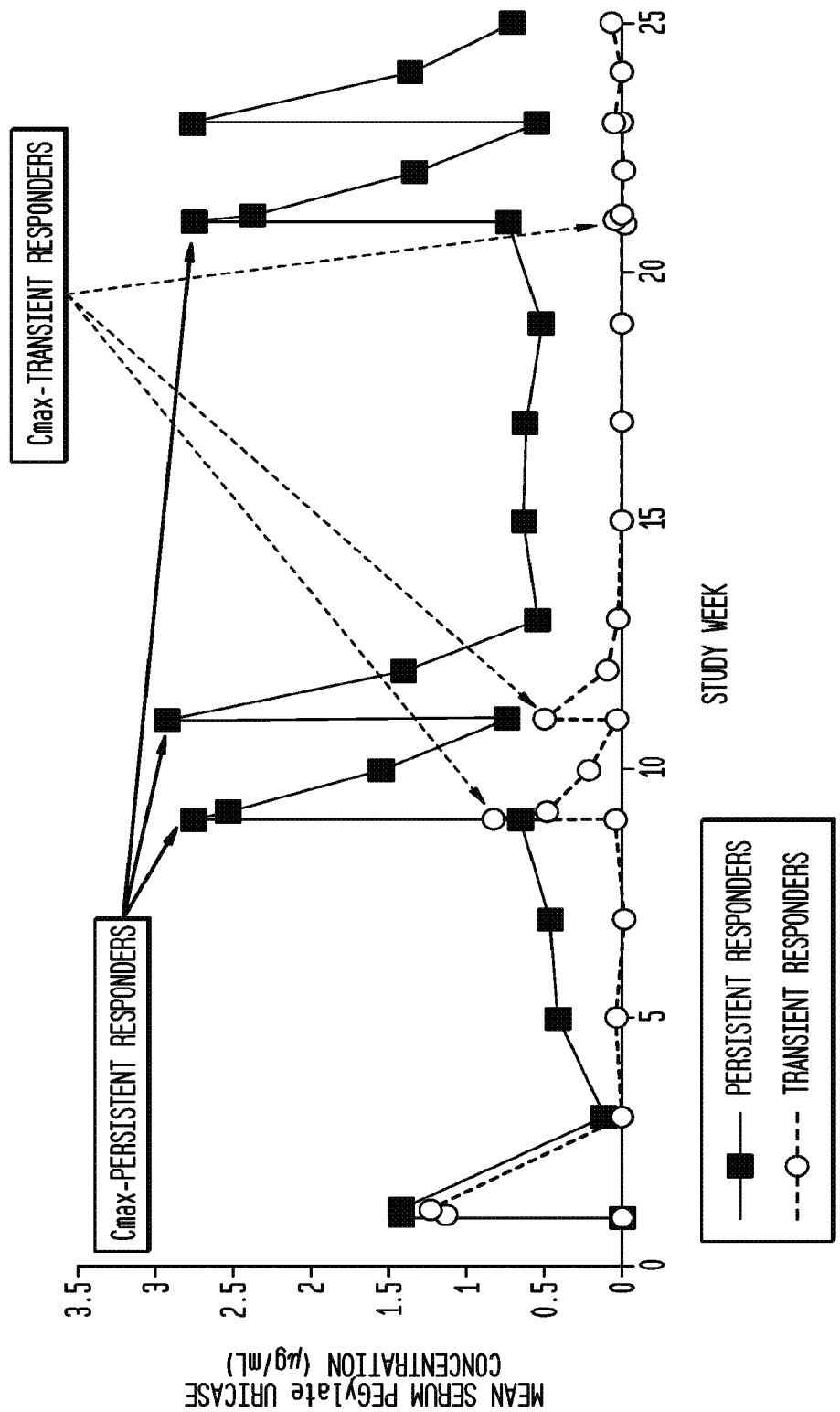
FIG. 2 shows time-concentration profile for pegloticase every 2 week administration.

As shown in FIG. 2, the pharmacokinetics of pegloticase administered every 2 weeks is significantly influenced by the presence of pegloticase antibodies. Persistent responders had higher pegloticase peak concentrations (Cmax) in both groups compared to transient responders. As shown in FIG. 2, transient responders in the q2 wk dose group showed decreased peak pegloticase concentrations after week 3. Further, by week 15, the transient responders had pegloticase concentrations that were below the level of detection (0.6 µg/mL). Persistent responders in the q2 wk group had pegloticase concentrations in the range of 0.5-0.7 µg/mL.

Figure 3:
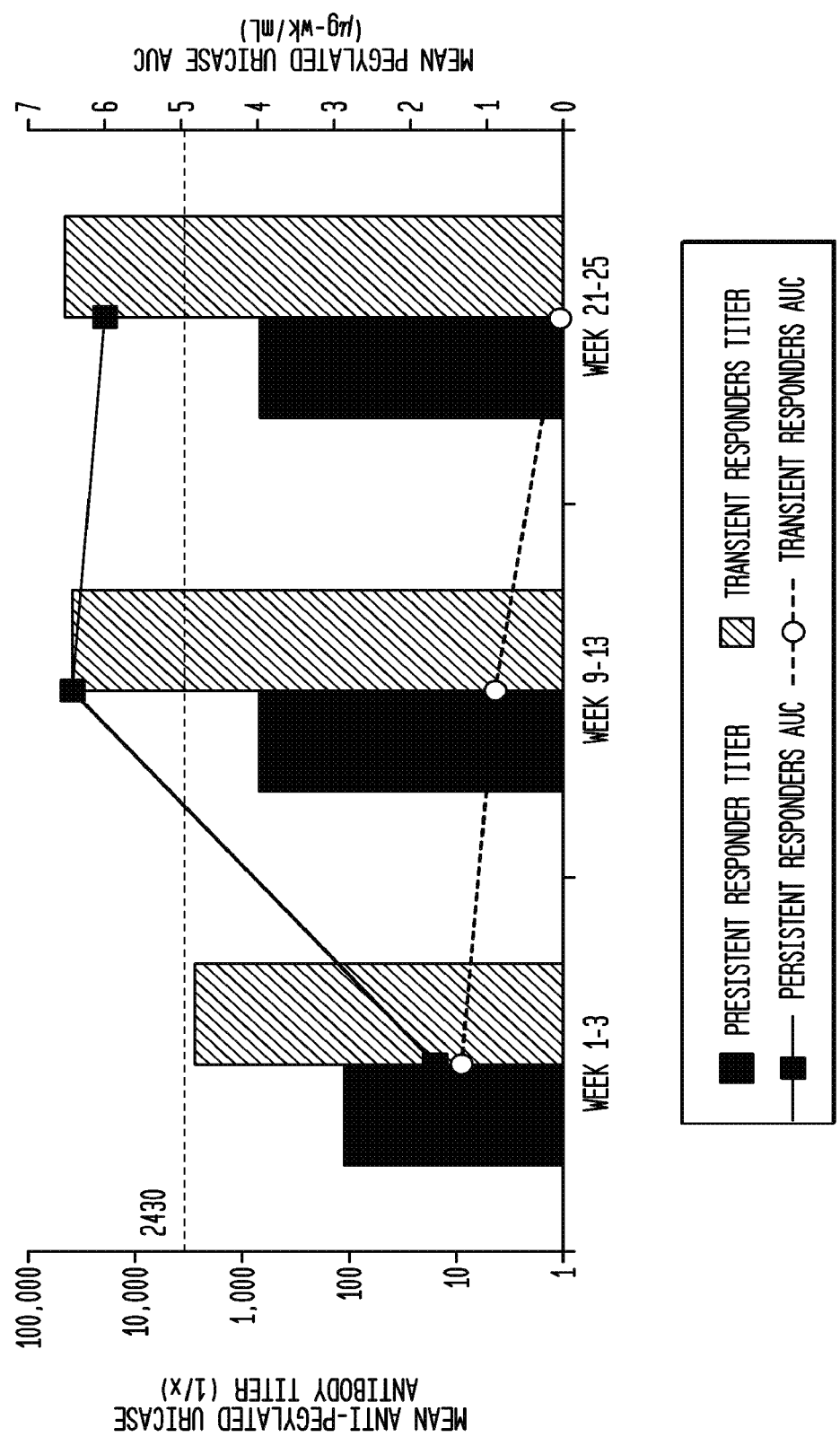
FIG. 3 shows relationship between antibody titer and AUC pegloticase every 2 week administration.

As shown in FIG. 3, in transient responders, the increased anti-pegloticase antibody titers were associated with markedly decreased pegloticase levels as assessed by the area under the time-concentration curve (AUC) compared with the pegloticase levels in the persistent responders. While there is an association between loss of response and development of higher pegloticase titers, loss of response could occur contemporaneously or even before the rise in antibody titer. Therefore, titer determinations are not predictive of loss of pegloticase response.

Anti-Pegloticase Antibody Effects on SUA/PUA Response: SUA/PUA as a Surrogate for Physiologically Relevant Anti-Pegloticase Antibodies.

Figure 4:
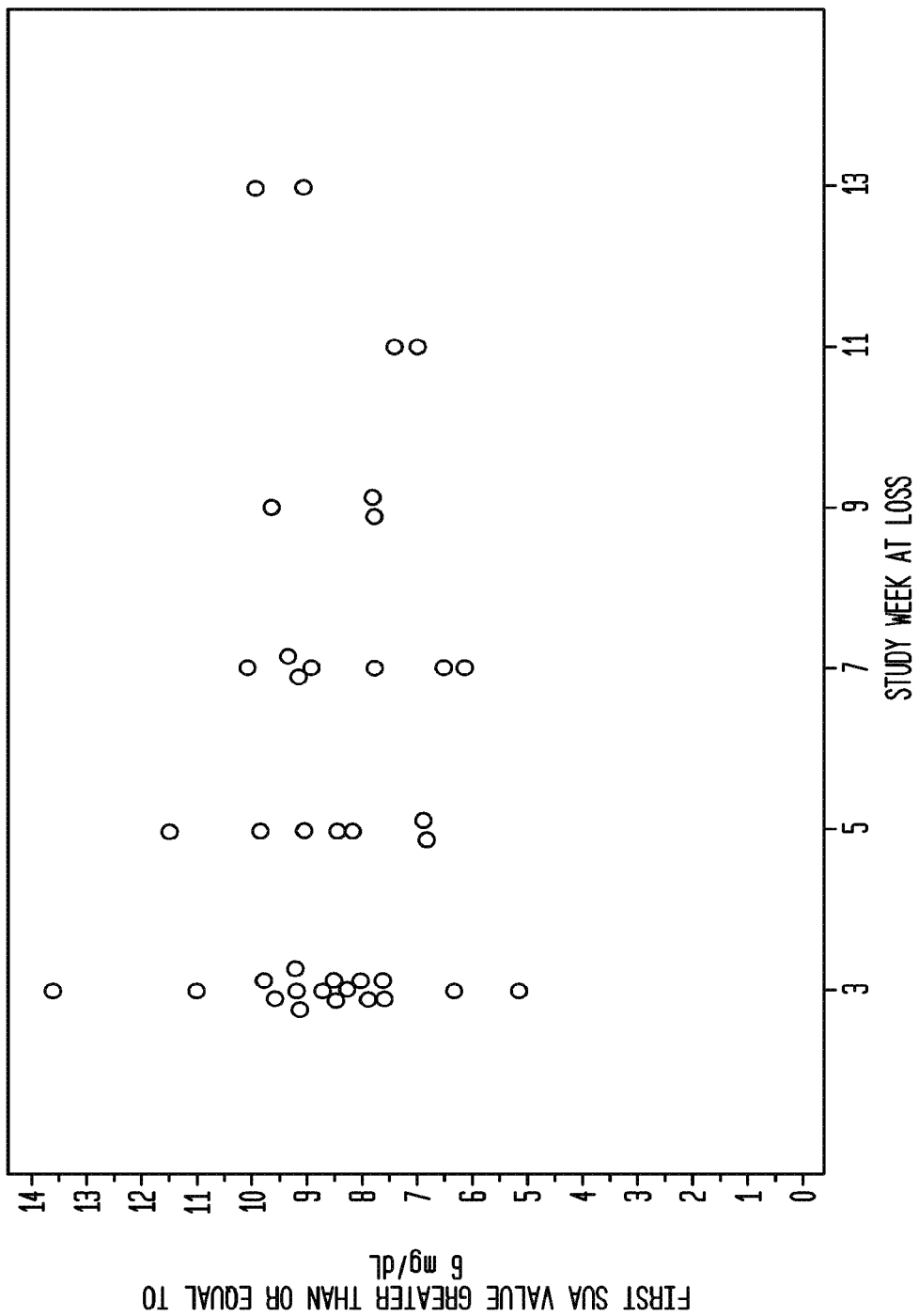
FIG. 4 shows SUA value at first detected loss response pegloticase every 2 weeks.
Figure 5:
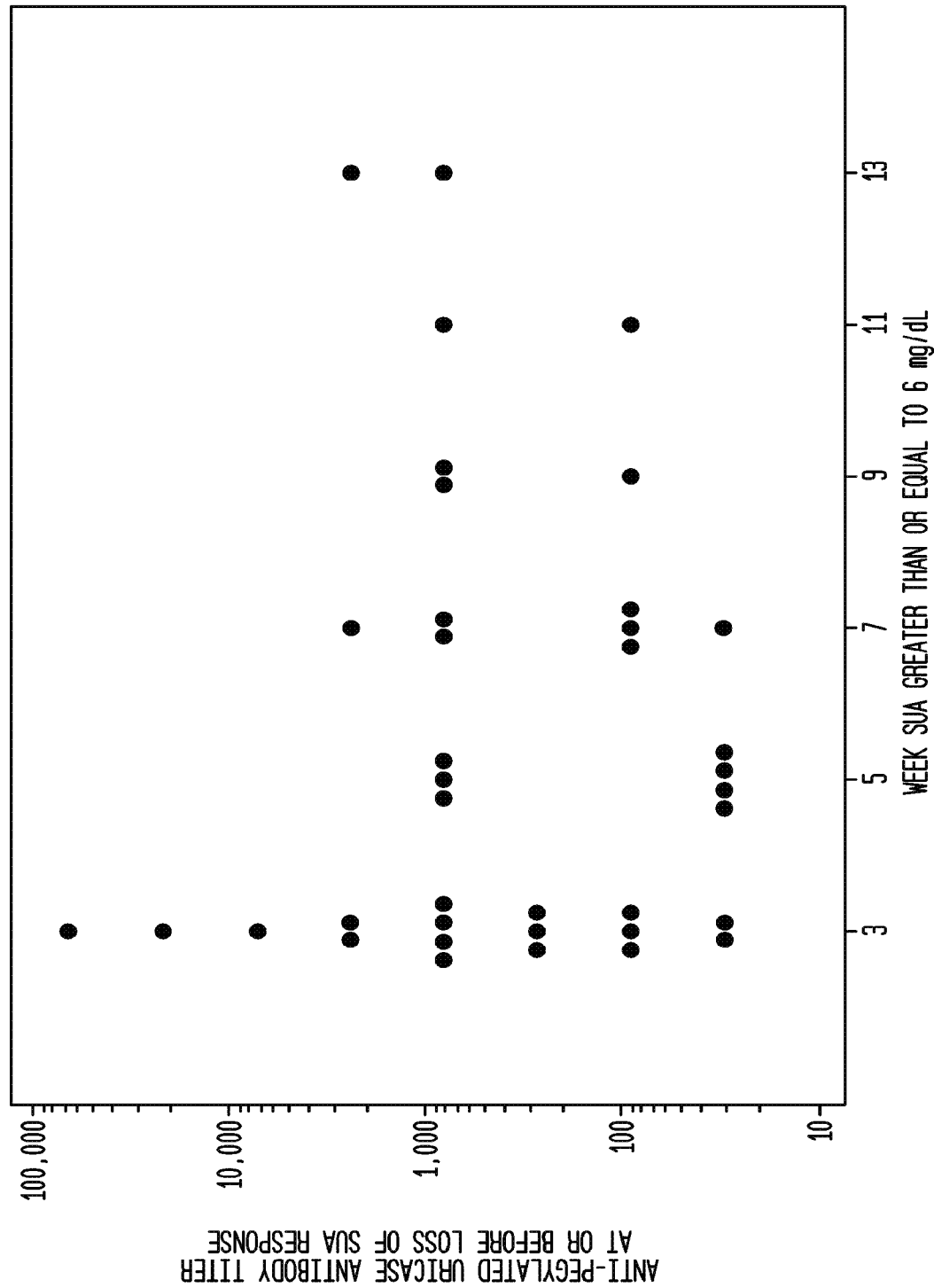
FIG. 5 shows anti-pegylated uricase antibody titer at time of loss of response pegloticase every 2 weeks.

It was further investigated when the SUA increase above 6 mg/dL occurred in the transient responder group following administration of pegloticase 8 mg q2 wks. Each point in the top panel of FIG. 4 represents the first measured SUA value that exceeded the threshold value of 6 mg/dL and the time at which this event occurred for each individual transient responder in the q2 wks group. FIG. 5 shows the corresponding antibody titers that were measured at or before the time of loss of uricase response. However, given that treatment with pegloticase q2 wks results in SUA values that are generally less than 3 mg/dL, the threshold SUA value representing a loss of pegloticase response can be set at an even lower value, for example between about 3.5 mg/dL to about 7 mg/dl. But as the rise in SUA due to loss of pegloticase response is generally rapid, 6 mg/dL is one of the accepted thresholds for control of uric acid by urate lowering drugs. However, 4 mg/dL and 5 mg/dL can be used successfully in these experiments as a threshold value for control of uric acid by urate lowering drugs.

At the time of loss of SUA normalization in the q2 wk group, i.e., when SUA exceeded 6 mg/dL, there was a wide range of anti-pegloticase antibody titers so that there appeared no threshold antibody titer that corresponded to this loss of response, as shown in FIG. 5. Specifically, at the time of loss of urate response, mean anti-pegloticase antibody titers were 1:3032 for the q2 wk group as compared to a mean highest titer of 1:686 for the q2 wk persistent responders.
Infusion Reaction and Loss of SUA Normalization.

Most patients (90.9%) had infusion reactions after pegloticase activity was lost, that is when SUA values were greater than or equal to 5 mg/dL (Table 1).

TABLE 1

SUA Category At Time of Infusion Reaction in Patients Receiving pegloticase Every 2 Weeks

| SUA Category | pegloticase 8 mg q2 wk n/N (%) | Placebo n/N (%) |
| --- | --- | --- |
| Number of Patients with IR when SUA ≥5 mg/dL | 20/22 (90.9) | 2/43 (4.7) |
| Number of Patients with IR when SUA <5 mg/dL | 1/22 (4.5) | 0 |
| Number of Patients with IR at First Dose | 1/22 (4.5) | 0 |

As shown in Table 1, in q2 wk group, 90.9% of infusion reactions would have been prevented if pegloticase therapy was discontinued at the time point when SUA≥5 mg/dL.

In summary, anti-pegloticase antibodies have direct effects on the pharmacokinetic and pharmacodynamic properties of pegloticase and explain the transient effect of pegloticase in the patients who develop physiologically-relevant antibodies. Although the increased clearance of pegloticase with the resultant loss of SUA/PUA response is mediated by anti-pegloticase antibodies, the initiation of increased clearance does not correlate with the anti-pegloticase antibody titer. Therefore, measurement of anti-pegloticase antibody titers is not predictive of the loss of the SUA/PUA response, whereas monitoring SUA/PUA is a very good surrogate for measuring the development of anti-pegloticase antibodies that cause increased clearance of administered pegloticase. Most importantly, monitoring SUA values, particularly during the first 4 months after initiating treatment with pegloticase, and stopping treatment with pegloticase when SUA values rise to levels greater than about 3.5 to 4 mg/dL is a simple method for identifying individuals who lose response to pegloticase and are at higher risk of experiencing an infusion reaction.

Example 2—Immunogenicity and Infusion Reaction Profiles of Phase III Clinical Study: Pegloticase Intravenous Administration at 8 mg Every 4 Weeks Clinical Study Using Infusion of Pegloticase.

A multicenter, randomized, double-blind placebo controlled clinical study was carried out as indicated in Example 1 above. Patients with hyperuricemia and gout received pegloticase 8 mg intravenously every 4 weeks (N=84) or placebo (N=43). Treatment was administered for 24 weeks.

Patients must have discontinued any uric acid-lowering agents for at least one week prior to receiving study drug, and refrain from using such agents throughout the study.

Anti-pegloticase antibodies were detected in 88% of patients in the pegloticase 8 mg q4 wk and in only 15% of the placebo group.

Figure 6:
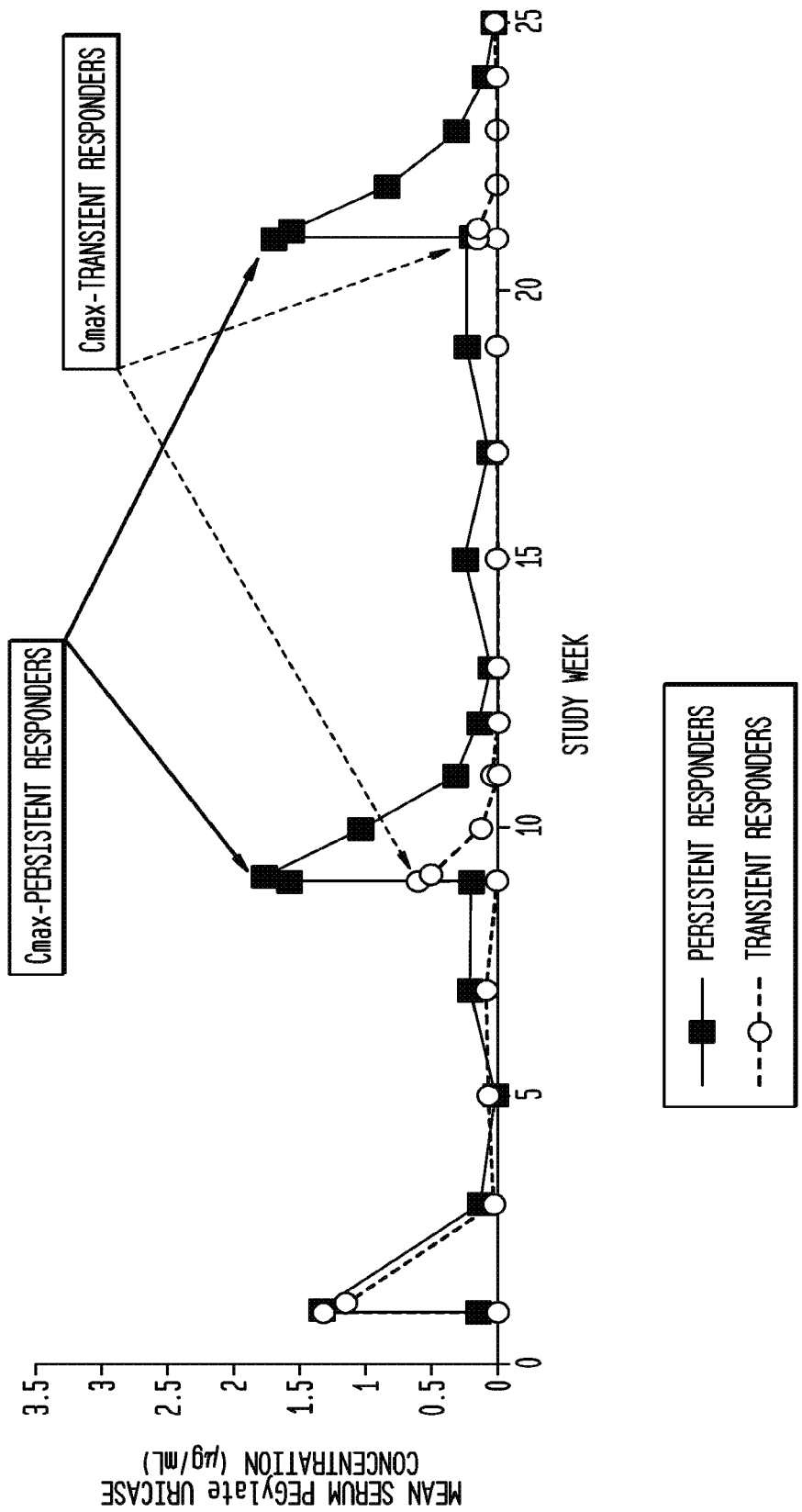
FIG. 6 shows time-concentration profile for pegloticase every 4 week administration.

As shown in FIG. 6, the pharmacokinetics of pegloticase administered every 4 weeks is significantly influenced by the presence of anti-pegloticase antibodies. Persistent responders had higher pegloticase peak concentrations (Cmax) in both groups compared to transient responders.

Table 2 shows that most patients (76.5%) who had an infusion reaction had SUA values at or above 6 mg/dL at the time the infusion reaction occurred. These infusion reactions could have been prevented if pegloticase was discontinued at the time point that SUA values were ≥6 mg/dL. Four patients had infusion reactions when SUA was less than 6 mg/dL and four patients who had an infusion reaction at first dose; none of these infusion reactions could have been prevented by monitoring SUA values.

TABLE 2

SUA Category at Time of Infusion Reaction in Patients Receiving pegloticase Every 4 Weeks

| SUA Category | pegloticase 8 mg q4 wk n/N (%) | Placebo n/N (%) |
|---|---|---|
| Number of Patients with IR when SUA ≥6 mg/dL | 26/34 (76.5) | 2/43 (4.7) |
| Number of Patients with IR when SUA <6 mg/dL | 4/34 (11.8) | 0 |
| Number of Patients with IR at First Dose | 4/34 (11.8) | 0 |

What is claimed is:

1. A method of treating a patient suffering from gout having a serum uric acid (SUA) level of 6 mg/dl or less and reducing the incidence of infusion reaction in the patient during PEGylated uricase therapy without measuring anti-PEGylated uricase and anti-PEG antibody titers, comprising the steps of:
   intravenously administering to said patient a therapeutically effective amount of PEGylated uricase every two weeks;
   obtaining a biological sample from said patient after a period of at least 2 weeks, wherein said biological sample is selected from the group consisting of blood, serum, and plasma;
   measuring a uric acid level in said biological sample; and
   indicating that the uric acid level is associated with a lower likelihood of antibody-mediated PEGylated uricase clearance when said uric acid level is maintained at less than 6 mg/dl or indicating that said uric acid level is associated with a higher likelihood of antibody-mediated PEGylated uricase clearance at a time point when said uric acid level is measured at least 6 mg/dl;
   if said uric acid level is less than 6 mg/dl then continuing said administration of PEGylated uricase every two weeks; or
   if said uric acid level is above 6 mg/dl then discontinuing said administration of PEGylated uricase every two weeks, thereby reducing the incidence of infusion reaction in said patient;
   wherein said patient previously received ineffective allopurinol therapy or has a medical history in which allopurinol therapy is contraindicated.

2. The method of claim 1, wherein said gout is refractory.

3. The method of claim 1, wherein said gout is chronic or tophaceous.

4. The method of claim 1, wherein the patient is administered one or more of fexofenadine, hydrocortisone, or acetaminophen, prior to each administration of PEGylated uricase.

5. The method of claim 1, wherein the infusion reaction comprises one or more of dyspnea, hypotension, hypertension, swelling, bronchospasm, chest pain, nausea, vomiting, or abdominal pain.

6. The method of claim 1, wherein the infusion reaction occurs within 2 hours of said intravenous administration of the PEGylated uricase.

7. The method of claim 1, wherein the PEGylated uricase comprises a mammalian uricase amino acid sequence truncated at the amino terminus or the carboxy terminus, or both the amino and the carboxy termini, by 1 to 13 amino acids, and further comprising an amino acid substitution at position 46, said truncation and amino acid substitution being relative to the native mammalian uricase amino acid sequence.

8. The method of claim 7, wherein the amino terminal amino acid is alanine, glycine, proline, serine, or threonine.

9. The method of claim 1, wherein the PEGylated uricase is pegloticase.

* * * * *